US012751606B2

(12) United States Patent
Visurraga, Jr.

(10) Patent No.: US 12,751,606 B2
(45) Date of Patent: Oct. 6, 2026

(54) MEDICAL VISUALIZATION AND INTUBATION SYSTEMS

(71) Applicant: Visurraga Enterprises, LLC, Hyattsville, MD (US)

(72) Inventor: Cesar Jesus Steven Visurraga, Jr., Hyattsville, MD (US)

(73) Assignee: Visurraga Enterprises, LLC, Hyattsville, MD (US)

( * ) Notice: Subject to any disclaimer, the term of this patent is extended or adjusted under 35 U.S.C. 154(b) by 0 days.

(21) Appl. No.: 19/002,073

(22) Filed: Dec. 26, 2024

(65) Prior Publication Data

US 2025/0120581 A1 Apr. 17, 2025

Related U.S. Application Data

(63) Continuation-in-part of application No. 18/522,902, filed on Nov. 29, 2023, now Pat. No. 12,539,026, and
(Continued)

(51) Int. Cl.
*A61B 1/267* (2006.01)
*A61B 1/00* (2006.01)
(Continued)

(52) U.S. Cl.
CPC ............ *A61B 1/05* (2013.01); *A61B 1/00052* (2013.01); *A61B 1/0008* (2013.01);
(Continued)

(58) Field of Classification Search
CPC . A61B 1/0655; A61B 1/00052; A61B 1/0008; A61B 1/00114; A61B 1/00124; A61B 1/0684; A61B 1/267; A61B 1/05
(Continued)

(56) References Cited

U.S. PATENT DOCUMENTS 6,115,523 A 9/2000 Choi et al.
6,319,195 B1 11/2001 Nakaichi et al.
(Continued)

FOREIGN PATENT DOCUMENTS

CN 203458664 U 3/2014
CN 103919522 A 7/2014
(Continued)

OTHER PUBLICATIONS

Https://aneskey.com/rigid-fiberoptic-and-video-laryngoscopes/, Jan. 20, 2019.
(Continued)

*Primary Examiner* — Jessica Weiss
(74) *Attorney, Agent, or Firm* — Leveque Intellectual Property Law, P.C.

(57) ABSTRACT

A laryngoscope enhancement system (LES) and an intubation system including an LES are provided. The LES includes a holder and a video stylet. The holder includes an adjustable mount to releasably secure an electronic device with a display, and an end cap configured to removably attach the holder to an upper end of a laryngoscope handle. The video stylet includes a connector removably attachable to the electronic device, a flexible segment, a malleable segment and a video camera. The LES may include wireless communication capabilities.

38 Claims, 30 Drawing Sheets

Related U.S. Application Data a continuation-in-part of application No. 18/522,876, filed on Nov. 29, 2023, now Pat. No. 12,539,025, said application No. 18/522,902 is a continuation of application No. 17/899,789, filed on Aug. 31, 2022, now Pat. No. 11,832,800.

(60) Provisional application No. 63/652,884, filed on May 29, 2024, provisional application No. 63/564,569, filed on Mar. 13, 2024, provisional application No. 63/615,458, filed on Dec. 28, 2023, provisional application No. 63/336,069, filed on Apr. 28, 2022, provisional application No. 63/267,779, filed on Feb. 9, 2022.

(51) Int. Cl.
*A61B 1/05* (2006.01)
*A61B 1/06* (2006.01)

(52) U.S. Cl.
CPC ...... *A61B 1/00114* (2013.01); *A61B 1/00124* (2013.01); *A61B 1/0655* (2022.02); *A61B 1/0684* (2013.01); *A61B 1/267* (2013.01)

(58) Field of Classification Search
USPC .................................. 600/101–114, 185–199
See application file for complete search history.

(56) References Cited

U.S. PATENT DOCUMENTS

| | | | | |
|---|---|---|---|---|
| 6,761,561 | B2 * | 7/2004 | Mandelkern | A61B 1/00016 433/29 |
| 7,946,981 | B1 | 5/2011 | Cubb | |
| 8,479,739 | B2 | 7/2013 | Hirsh | |
| 8,652,033 | B2 * | 2/2014 | Berci | A61B 1/0005 600/199 |
| 8,721,535 | B2 | 5/2014 | Chen | |
| 8,777,848 | B2 | 7/2014 | Dhonneur | |
| D724,725 | S | 3/2015 | Chang | |
| 8,972,714 | B2 | 3/2015 | Talbert et al. | |
| 9,179,831 | B2 | 11/2015 | McGrail et al. | |
| 9,199,051 | B2 | 12/2015 | Booth | |
| 9,295,378 | B2 | 3/2016 | Nearman et al. | |
| 9,351,633 | B2 | 5/2016 | Tydlaska et al. | |
| 9,427,543 | B2 | 8/2016 | Wei et al. | |
| 9,579,476 | B2 | 2/2017 | Stocking et al. | |
| 9,662,466 | B2 | 5/2017 | Gunday et al. | |
| 9,681,797 | B2 | 6/2017 | Scherr et al. | |
| 9,782,061 | B2 | 10/2017 | Newcomb et al. | |
| 10,182,712 | B2 | 1/2019 | Matthes | |
| 10,285,580 | B2 | 5/2019 | Brambrink et al. | |
| 10,368,732 | B2 | 8/2019 | Law et al. | |
| 10,588,498 | B2 | 3/2020 | Dan et al. | |
| 10,729,317 | B2 | 8/2020 | Eggli et al. | |
| 10,744,288 | B2 | 8/2020 | Runnels | |
| 11,064,877 | B2 | 7/2021 | Galloway et al. | |
| 11,517,181 | B2 | 12/2022 | Podpolucha et al. | |
| 11,832,800 | B2 | 12/2023 | Visurraga, Jr. | |
| 11,839,354 | B2 | 12/2023 | Sabetrasekh et al. | |
| 11,925,331 | B2 | 3/2024 | Gonsowski | |
| 2002/0022769 | A1 | 2/2002 | Smith et al. | |
| 2003/0195390 | A1 | 10/2003 | Graumann | |
| 2005/0182297 | A1 | 8/2005 | Gravenstein et al. | |
| 2006/0004260 | A1 | 1/2006 | Boedeker et al. | |
| 2007/0179342 | A1 * | 8/2007 | Miller | A61B 1/05 600/199 |
| 2008/0064926 | A1 * | 3/2008 | Chen | A61B 1/267 600/110 |
| 2009/0032016 | A1 | 2/2009 | Law et al. | |
| 2009/0192350 | A1 * | 7/2009 | Mejia | A61B 1/042 600/109 |
| 2009/0247833 | A1 * | 10/2009 | Tanaka | G09B 23/285 600/188 |
| 2010/0168521 | A1 | 7/2010 | Acha Gandarias | |
| 2010/0261967 | A1 | 10/2010 | Pacey et al. | |
| 2010/0312059 | A1 | 12/2010 | Mcgrath | |
| 2011/0009694 | A1 | 1/2011 | Schultz et al. | |
| 2011/0028790 | A1 * | 2/2011 | Farr | A61B 1/0676 600/187 |
| 2011/0130632 | A1 | 6/2011 | McGrail et al. | |
| 2011/0137127 | A1 | 6/2011 | Schwartz et al. | |
| 2011/0152620 | A1 * | 6/2011 | Dhonneur | A61M 16/0493 600/194 |
| 2011/0160537 | A1 | 6/2011 | Chen | |
| 2011/0178372 | A1 | 7/2011 | Pacey et al. | |
| 2011/0178373 | A1 | 7/2011 | Pacey et al. | |
| 2011/0245609 | A1 * | 10/2011 | Laser | A61B 1/00052 600/109 |
| 2012/0078055 | A1 | 3/2012 | Berci et al. | |
| 2012/0162401 | A1 | 6/2012 | Melder et al. | |
| 2013/0096378 | A1 * | 4/2013 | Alexander | A61B 1/0014 606/191 |
| 2014/0160261 | A1 * | 6/2014 | Miller | A61B 1/05 348/77 |
| 2014/0194694 | A1 | 7/2014 | Chen | |
| 2015/0151063 | A1 * | 6/2015 | Hoftman | A61B 1/05 128/200.26 |
| 2015/0190044 | A1 | 7/2015 | Livnat | |
| 2016/0051781 | A1 | 2/2016 | Isaacs | |
| 2016/0206189 | A1 | 7/2016 | Nearman et al. | |
| 2018/0168433 | A1 | 6/2018 | Meyer et al. | |
| 2018/0184892 | A1 | 7/2018 | Truckai et al. | |
| 2020/0178786 | A1 | 6/2020 | Sabetrasekh et al. | |
| 2020/0359883 | A1 | 11/2020 | Livnat | |
| 2021/0219834 | A1 | 7/2021 | Velez Rivera | |
| 2021/0220594 | A1 | 7/2021 | Biro et al. | |
| 2022/0104884 | A1 | 4/2022 | Leiderman et al. | |
| 2022/0110504 | A1 | 4/2022 | Inglis | |
| 2022/0257092 | A1 | 8/2022 | Ng et al. | |
| 2022/0257889 | A1 | 8/2022 | Alonso Babarro | |
| 2023/0137933 | A1 | 5/2023 | Gros et al. | |
| 2023/0248235 | A1 * | 8/2023 | Ng | A61B 1/00048 600/188 |
| 2023/0255465 | A1 | 8/2023 | Gaffney, II | |
| 2024/0008732 | A1 | 1/2024 | Huang et al. | |
| 2024/0090757 | A1 | 3/2024 | Visurraga, Jr. | |
| 2024/0090758 | A1 | 3/2024 | Visurraga, Jr. | |
| 2024/0252775 | A1 | 8/2024 | Gage et al. | |

FOREIGN PATENT DOCUMENTS

| | | | |
|---|---|---|---|
| CN | 104161494 | A | 11/2014 |
| CN | 204033305 | U | 12/2014 |
| CN | 105725959 | A | 7/2016 |
| CN | 206372368 | U | 8/2017 |
| CN | 112603237 | B | 4/2021 |
| DE | 202014106287 | U1 | 2/2015 |
| EP | 3111827 | A1 | 1/2017 |
| JP | 3108837 | U | 3/2005 |
| JP | 3198848 | U | 7/2015 |
| JP | 2020072930 | A | 5/2020 |
| WO | 2010123858 | A2 | 10/2010 |
| WO | 2011128610 | A1 | 10/2011 |
| WO | 2012097181 | A1 | 7/2012 |
| WO | 2018100587 | A1 | 6/2018 |
| WO | 2020003192 | A1 | 1/2020 |
| WO | 2020210327 | A1 | 10/2020 |
| WO | 2021170626 | A1 | 9/2021 |
| WO | 2021234196 | A1 | 11/2021 |
| WO | 2023033665 | A1 | 3/2023 |
| WO | 2023212085 | A1 | 11/2023 |

OTHER PUBLICATIONS

Https://cults3d.com/en/3d-model/tool/video-laringoscope, downloaded from internet Mar. 9, 2023.

Https://flexicare.com/product/provu-video-stylet/, downloaded from the internet on Apr. 8, 2025.

Https://smartblade.co.za/, downloaded from the internet on Mar. 9, 2023.

(56) References Cited

OTHER PUBLICATIONS

Https://www.aummedtech.com/video-laryngoscopes-covid-warriors/, downloaded from the internet on Mar. 9, 2023.
Https://www.hullanesthesia.com/p/1031/ainca-video-stylet-with-monitor-and-charger, Downloaded from the internet on Mar. 9, 2023.
Https://www.imedicalapps.com/2016/04/iphone-intubation-video-laryngoscopy-vlstreaming-adaptor/, downloaded from the internet on Mar. 9, 2023.
Https://www.marketlab.com/product/Malleable-Video-Stylet-ML16971, downloaded from the internet on Apr. 8, 2025.
Matek J, Kolek F, Klementova O, Michalek P, Vymazal T. Optical Devices in Tracheal Intubation-State of the Art in 2020. Diagnostics (Basel). Mar. 22, 2021;11(3):575. doi: 10.3390/diagnostics11030575. PMID: 33810158; PMCID: PMC8004982.
Sanitas, Protectscope Instruction Manual, Feb. 2021.

* cited by examiner

Example 1

Cross Section

MEDICAL VISUALIZATION AND INTUBATION SYSTEMS

CROSS-REFERENCE TO RELATED APPLICATIONS

This application is a continuation-in-part of U.S. patents application Ser. Nos. 18/522,876 and 18/522,902 (filed on Nov. 29, 2023) which are continuations of U.S. patent application Ser. No. 17/899,789 (filed on Apr. 28, 2022), now U.S. Pat. No. 11,832,800,which claims the benefit of U.S. Provisional Patent Application Nos. 63/336,069 (filed on Apr. 28, 2022) and 63/267,779 (filed on Feb. 9, 2022) the contents of which are incorporated herein by reference in their entireties. This application claims the benefit of U.S. Provisional Patent Application Nos. 63/652,884 (filed on May 29, 2024), 63/564,569 (filed on Mar. 13, 2024) and 63/615,458 (filed on Dec. 28, 2023) the contents of which are incorporated herein by reference in their entireties.

BACKGROUND

The present disclosure relates to medical devices. More particularly, the present disclosure relates to a medical visualization and intubation systems.

Laryngoscopy may be performed for many reasons, such as, for example, to view the interior structure of the throat such as the larynx, to facilitate endotracheal intubation using an endotracheal tube (ETT), to perform a biopsy procedure, etc. Generally, direct laryngoscopy refers to the use of a handheld laryngoscope to view the interior structure of the throat along a direct line-of-sight, while indirect laryngoscopy refers to the use of a laryngoscope in combination with an optical device to visualize the larynx or trachea along an indirect line-of-sight, such as, for example, a mirror or prism, a fiberoptic stylet, a video laryngoscope, etc.

However, for certain medical procedures, direct laryngoscopy often presents challenges that make a direct line-of-sight view difficult due to planned or unplanned scenarios such as anterior vocal cords, obesity, large tongue, or other irregular airway anatomical features.

DETAILED DESCRIPTION

Figure 1:
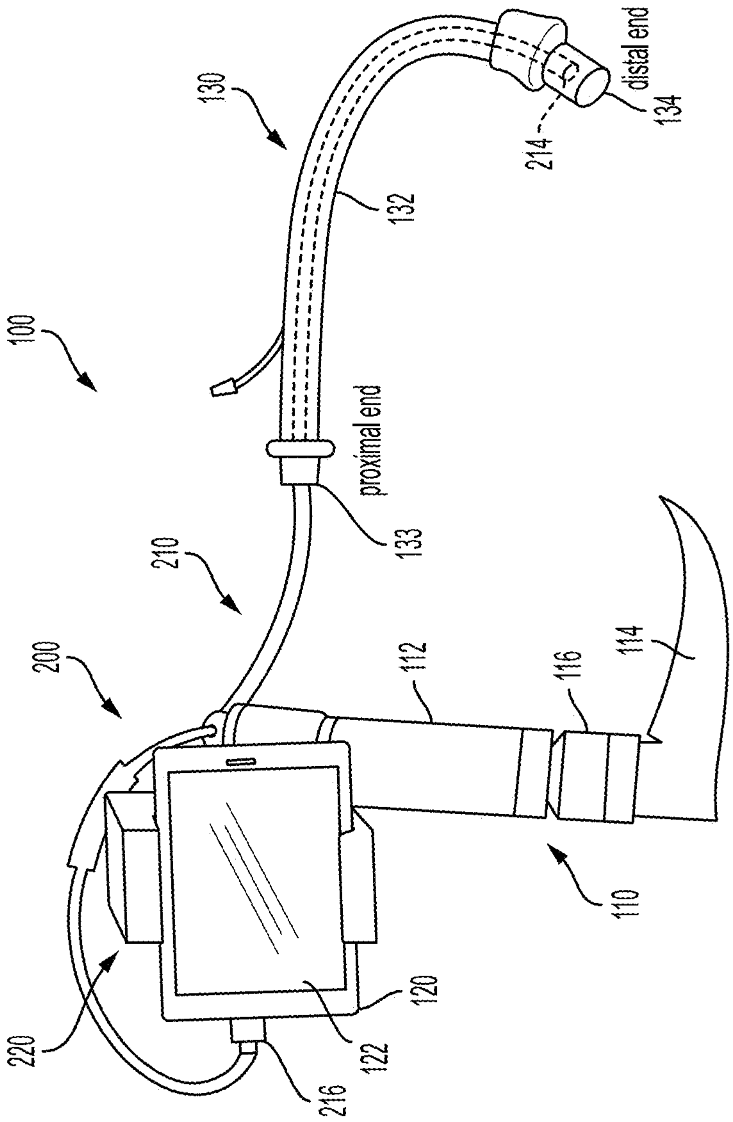
FIG. 1 depicts an intubation system (IS), in accordance with an embodiment of the present disclosure.

Embodiments of the present disclosure will now be described with reference to the drawing figures, in which like reference numerals refer to like parts throughout.

Embodiments of the present disclosure advantageously provide a system that broadens the use of a standard laryngoscope beyond direct laryngoscopy to video-based, indirect laryngoscopy for various medical procedures, such as, for example, intubation, visualization, etc.

In one embodiment, a laryngoscope enhancement system includes a holder and a video stylet. The holder includes a mount to accommodate different sizes and configurations of an electronic device, and an end cap. The mount is configured to releasably secure an electronic device with a display and may be an adjustable mount that is adjustable to accommodate different sizes and configurations of an electronic device. The end cap is fixedly connected to the adjustable mount, and defines a central cavity with a lower opening. The end cap is configured to removably attach the holder to an upper end of a laryngoscope handle, and the lower opening has a diameter conforming to a diameter of the upper end of the laryngoscope handle. The video stylet includes a number of wires, a connecter coupled to the wires, a flexible segment, a malleable segment and a video camera coupled to one or more of the wires. The connector is removably attachable to an electronic device. The flexible segment includes a flexible sheath enclosing the wires. The malleable segment includes a malleable sheath enclosing a malleable wire and the wires. The malleable sheath has a smaller diameter than the flexible sheath.

FIG. 1 depicts IS 100, in accordance with an embodiment of the present disclosure.

In many embodiments, IS 100 includes laryngoscope 110, electronic device 120, ETT 130 and LES 200.

Laryngoscope 110 includes handle 112, blade 114 and connector 116 that attaches blade 114 to the lower end of handle 112. Connector 116 may be fixed, or releasable in order to support different sizes and types of blades 114. For example, a portion of connector 116 may be fixed to, or incorporated within, the lower end of handle 112, a mating portion of connector 116 may be fixed to, or incorporated within, the proximal end of blade 114. Blade 114 may be a Macintosh (curved) blade, a Miller (straight) blade, etc., and generally includes a spatula to pass over the lingual surface of the tongue, a flange to displace the tongue, and a tip to lift the epiglottis. Handle 112 is cylindrical in shape with a generally uniform diameter, and has an upper end as well as the lower end.

Electronic device 120 includes display 122 for displaying images from video stylet 210. More particularly, electronic device 120 is a portable, handheld, computer-based electronic device with a touchscreen interface and a data/charging port (e.g., a Lighting port, a USB-C port, etc.), such as, for example, a smartphone (e.g., Apple iPhone, Samsung Galaxy S/A/Z, etc.), a tablet (e.g., Apple iPad mini, Samsung Galaxy Tab, etc.), etc. In some embodiments, electronic device 120 may include a network interface to connect to a cellular network, a Wi-Fi network, etc. Further, it is envisioned that the user can connect to laptops, desktops, etc. via a USB port.

ETT 130 includes, inter alia, tube 132, proximal endcap 133 defining a proximal opening, and beveled distal end 134 defining a distal opening.

LES 200 includes video stylet 210 and a device mount or holder 220 for electronic device 120. Video stylet 210 includes, inter alia, connector 216 that is removably attachable to the data/charging port of electronic device 120, a flexible segment (depicted in solid line) generally disposed outside tube 132, a malleable segment (depicted in dotted line) generally disposed within tube 132, and video camera 214. The malleable segment of video stylet 210 is deformable into a preferred shape or curvature, and may extend past the proximal end of ETT 130, i.e., outside tube 132. The combination of a flexible segment and a malleable segment in video stylet 210 is advantageously lightweight and maneuvers easily when advancing ETT 130 into the patient's airway with one hand.

Figure 2:
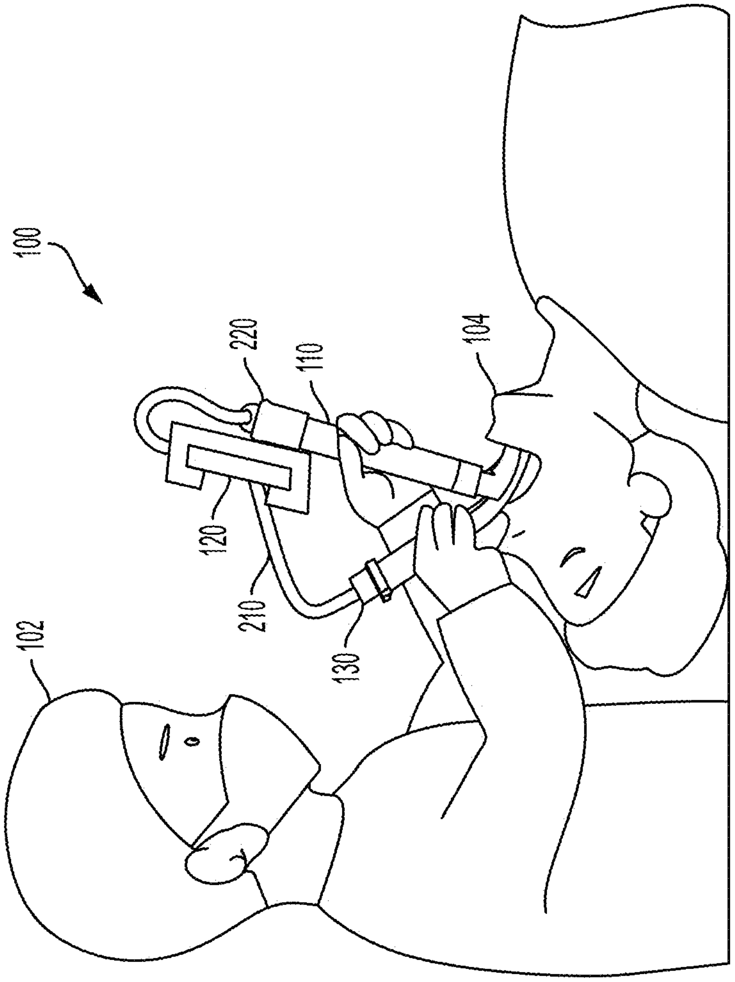
FIG. 2 depicts in-situ operation of an IS, in accordance with an embodiment of the present disclosure.

FIG. 2 depicts in-situ operation of IS 100, in accordance with an embodiment of the present disclosure.

During an intubation procedure for patient 104, healthcare provider 102 holds handle 112 of laryngoscope 110 in one hand and tube 132 of ETT 130 in the other hand. More particularly, healthcare provider 102 first manipulates video stylet 210 into a preferred curvature, and then inserts video stylet 210 into the opening defined by proximal endcap 133 of ETT 130 such that video camera 214 is disposed proximate to the opening defined by beveled distal end 134 of ETT 130. Once inserted, ETT 130 generally conforms to the curvature of the malleable portion of video stylet 210. With the assistance of laryngoscope 110, healthcare provider 102 introduces ETT 130 into the mouth of patient 104. After initially positioning ETT 130, healthcare provider 102 then advances ETT 130 towards the vocal cords of patient 104 using indirect laryngoscopy, during which time images of the upper airway, captured by video camera 214, are presented on display 122 for viewing by healthcare provider 102.

During a visualization procedure for patient 104, ETT 130 is not used and healthcare provider 102 holds handle 112 of laryngoscope 110 in one hand and video stylet 210 in the other hand. More particularly, with the assistance of laryngoscope 110, healthcare provider 102 introduces video stylet 210 into the mouth of patient 104. After initially positioning video stylet 210, healthcare provider 102 then advances video stylet 210 towards the vocal cords of patient 104 using indirect laryngoscopy, during which time images of the upper airway, captured by video camera 214, are presented on display 122 for viewing by healthcare provider 102.

IS 100 advantageously incorporates the same handheld laryngoscope into these procedures, which allows healthcare provider 102 to perform the same physical movements as before while integrating indirect line-of-sight capability.

Figure 3:
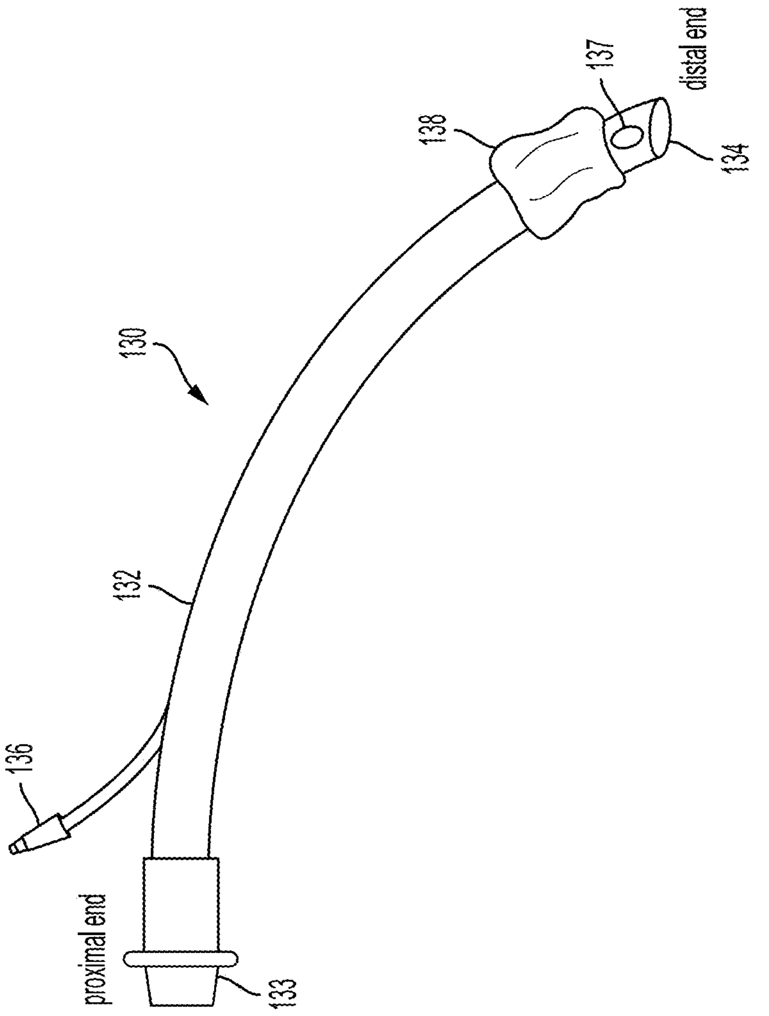
FIG. 3 depicts an ETT, in accordance with an embodiment of the present disclosure.

FIG. 3 depicts ETT 130, in accordance with an embodiment of the present disclosure.

ETT 130 includes tube 132, proximal endcap 133 defining a proximal opening, beveled distal end 134 defining a distal opening, air supply connector 136, and inflatable cuff/balloon 138. Opening 137 (e.g., a "Murphy eye") may also be provided at the distal end of tube 132 to prevent obstruction if the distal opening defined by beveled distal end 134 is blocked by mucus or sealed by contact with the patient's tracheal wall.

The proximal opening accepts video stylet 210 for passage through tube 132, while the distal opening allows video camera 214 to extend past beveled distal end 134 (if desired). Generally, tube 132 has an outer diameter and an inner diameter, and ETT 130 has a size (in millimeters) that is based on the inner diameter of tube 132, generally ranging from 3.5 (i.e., 3.5 mm inner diameter, e.g., for small infants) to 8.5 (i.e., 8.5 mm inner diameter, e.g., for adult males), and larger. The sizes are typically specified in 0.5 mm increments.

Figure 4:
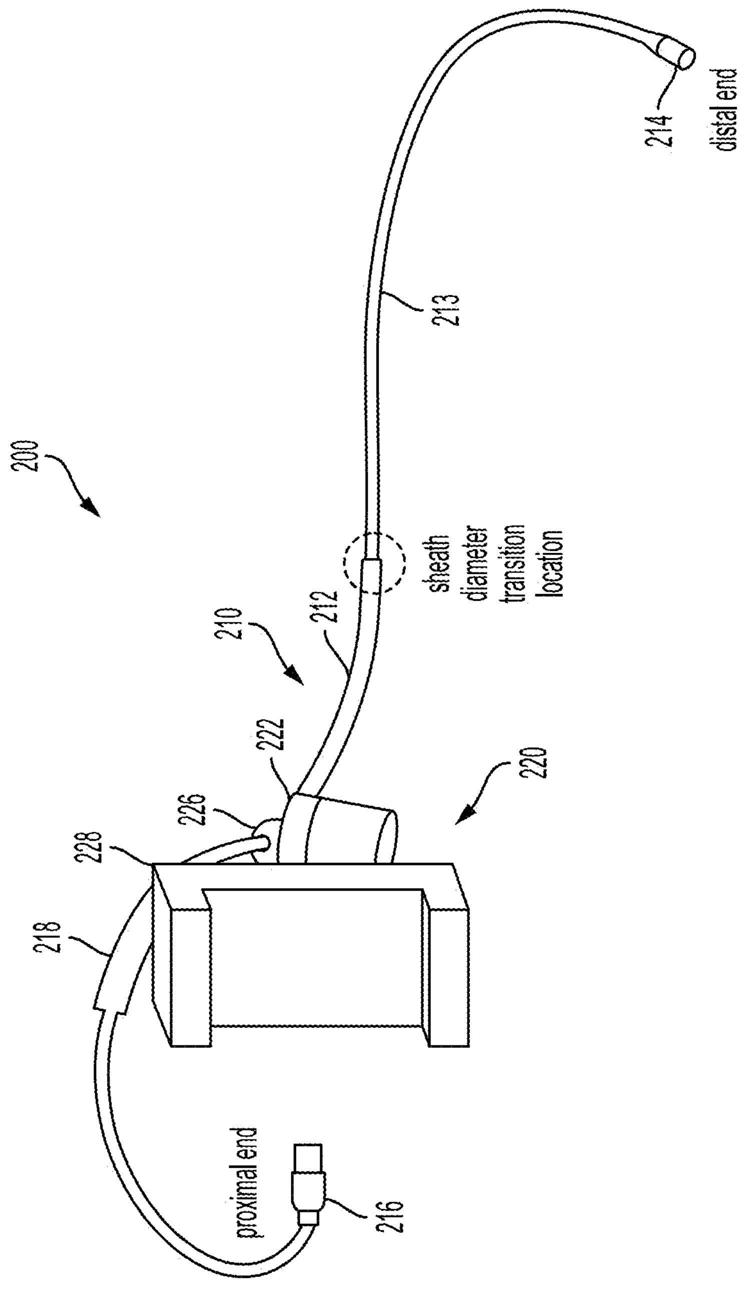
FIG. 4 depicts a laryngoscope enhancement system (LES), in accordance with an embodiment of the present disclosure.

FIG. 4 depicts LES 200, in accordance with an embodiment of the present disclosure.

LES 200 includes video stylet 210 and holder 220 for electronic device 120.

Generally, video stylet 210 includes connector 216 that is removably attachable to the data/charging port of electronic device 120, a flexible portion, i.e., tube or sheath 212, a malleable portion, i.e., tube or sheath 213, and video camera 214. In many embodiments, a light source (not depicted for clarity) may be co-located with video camera 214. In certain embodiments, light source control unit 218 is coupled to one or more of the wires to control the light source, such as, for example, one or more light-emitting diodes (LEDs), etc. Light source control unit 218 may include a dial, button(s), slider, etc. to control the intensity of the light source.

Holder 220 includes end cap 222 and adjustable mount 228. In many embodiments, holder 220 may also include guide 226 to support a portion of video stylet 210. In the embodiment depicted in FIG. 4, guide 226 is disposed on an upper portion of end cap 222; other locations are also supported.

Figure 5A:
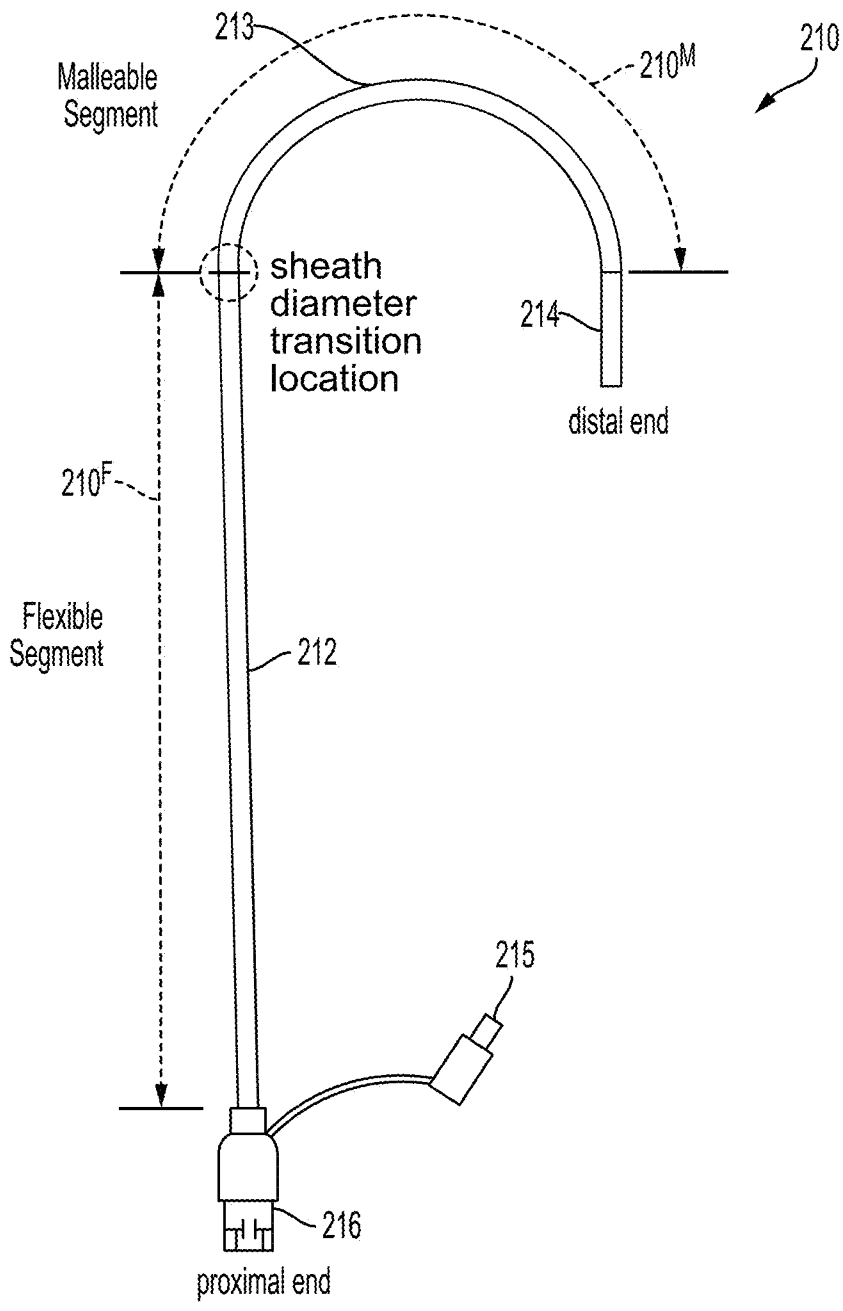
FIGS. 5A, 5B and 5C depict a video stylet of an LES, in accordance with an embodiment of the present disclosure.
Figure 5B:
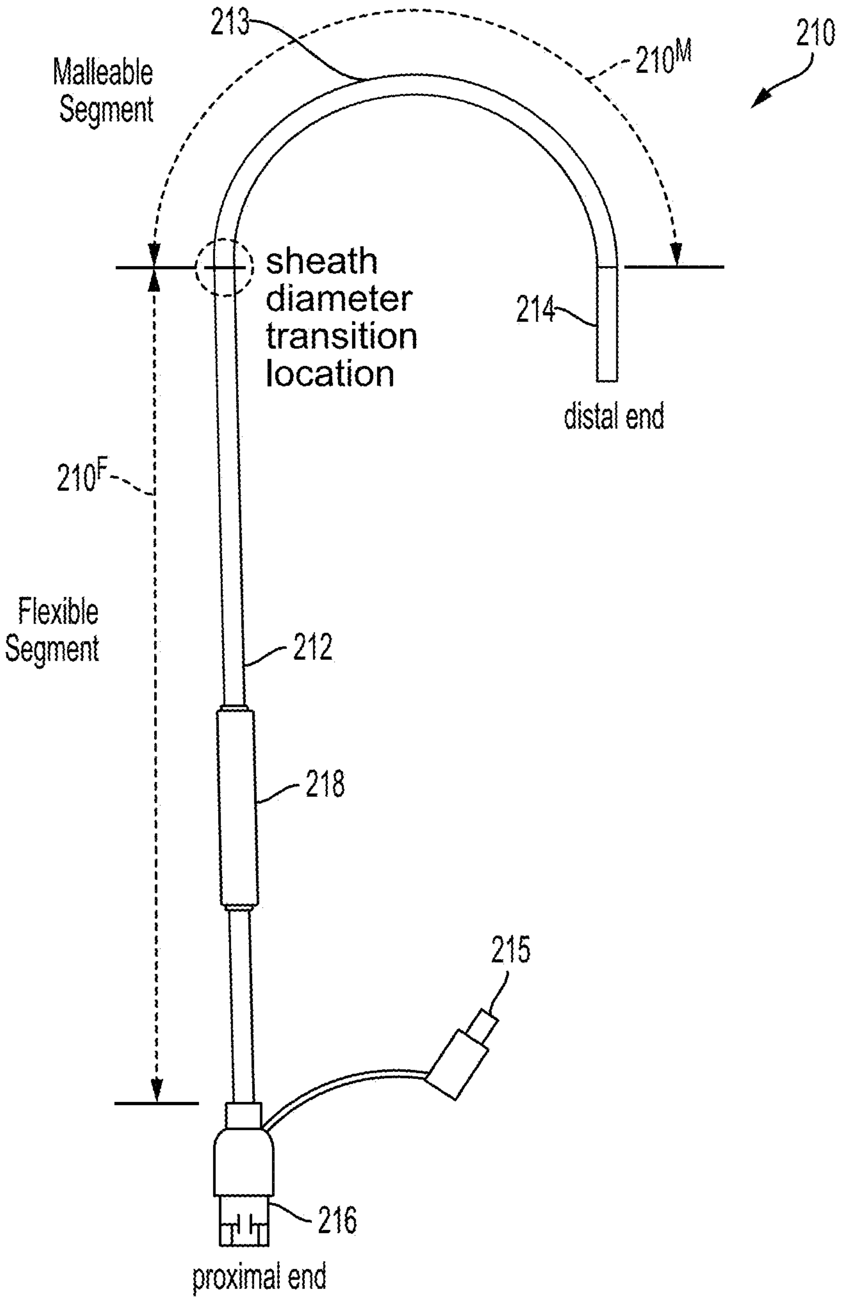
Figure 5C:
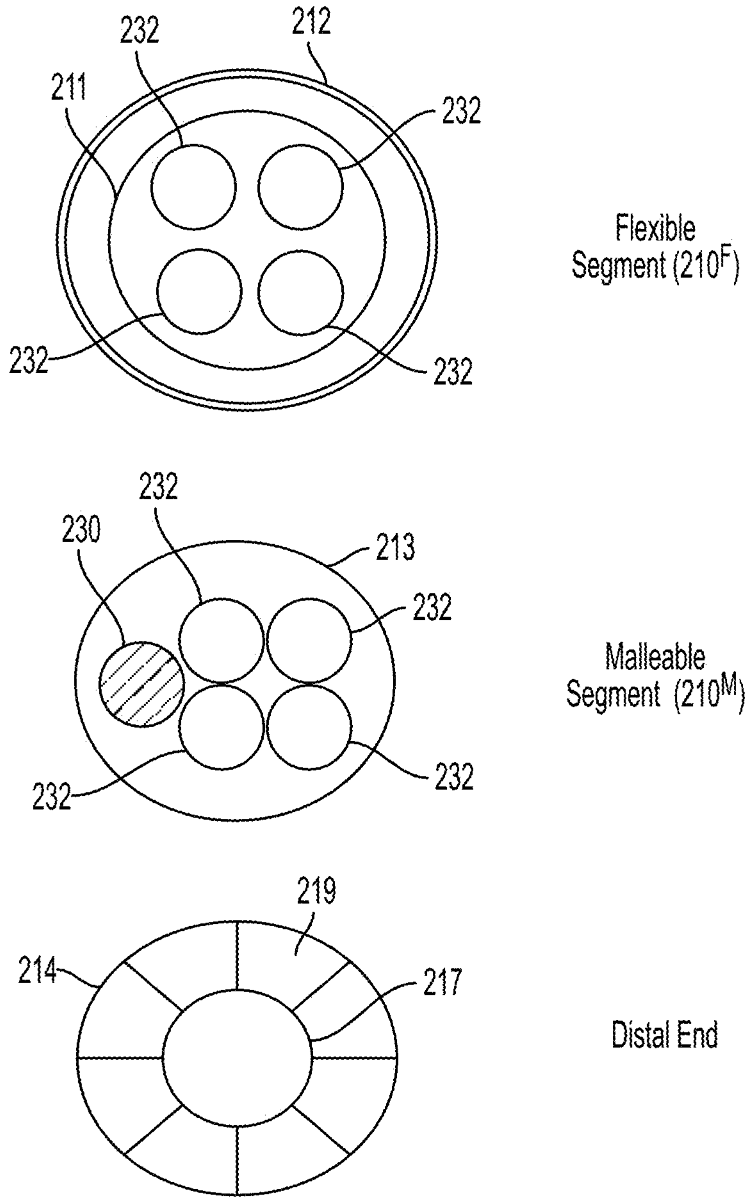

FIGS. 5A, 5B and 5C depict video stylet 210, in accordance with embodiments of the present disclosure.

More particularly, FIGS. 5A and 5B depict plan views of video stylet 210, in accordance with embodiments of the present disclosure, while FIG. 5C depicts a cross-sectional view of the flexible segment of video stylet 210, a cross-sectional view of the malleable segment of video stylet 210, and a view of the distal end of video stylet 210, in accordance with embodiments of the present disclosure.

Video stylet 210 has a proximal end, flexible segment 210, a sheath diameter transition location, a malleable segment 210M, and a distal end. In many embodiments, video stylet has an overall length of about 33 to 42 inches, flexible segment 210F has a diameter of about 7 to 12 mm and a length of about 16 to 20 inches, malleable segment 210M has a diameter of about 3 to 6.5 mm and a length of about 16 to 20 inches, and video camera 214 has a diameter of about 3 to 5.5 mm and a length of about 1 to 2 inches.

A number of wires 232 couple connector 216 to video camera 214, and extend through flexible segment 210F and malleable segment 210M. Generally, the number of wires 232 are determined by a particular electrical communication specification, such as, for example, Universal Serial Bus (USB), etc. Connector 216 is coupled to the wires at the proximal end of video stylet 210. Sheath 212 encloses the wires, and extends along the length of flexible segment 210F, i.e., from connector 216 to the sheath diameter transition location. Sheath 213 encloses a malleable wire and the wires, and extends along the length of malleable segment 210M, i.e., from the sheath diameter transition location to the video camera 214. Advantageously, sheath 213 has a smaller diameter than sheath 212 to accommodate small diameter ETTs 130.

In certain embodiments, an additional connector 215 may be coupled the wires at the proximal end of video stylet 210. Additional connector 215 may have a different electrical interface than connector 216, and may be coupled to an additional electronic device, such as, for example, a smartphone, tablet, large screen monitor, etc. In other embodiments, the electrical interfaces may be the same for connectors 215 and 216. The electrical interfaces may be either or both wireless, using, for example, Wi-Fi technology such as, for example, a built-in Wi-Fi capacity for wireless connectivity.

Video camera 214 is coupled to the wires at the distal end of video stylet 210. In many embodiments, a light source (not depicted for clarity) may be co-located with video camera 214 and coupled to the wires. In certain embodiments, light source control unit 218 is coupled to one or more of the wires to control the light source, such as, for example, one or more light-emitting diodes (LEDs), etc.

The cross section for flexible segment 210F depicts sheath 212, shield 211 and wires 232. Sheath 212 made be manufactured from solid polyvinyl chloride (PVC) to protect the cables from damage, such as, for example, fraying, etc. Shield 211 may include one or more layers of wire, aluminum foil and/or mylar. Wires 232 may be single or multiple strands of copper wire that are clad with high-resistance insulation material, such as, for example, a dielectric material, etc.; certain wires may be unclad. In many embodiments, the wires include a ground wire, a power wire, and two or more signal wires; the signal wires may be untwisted or twisted pairs.

The cross section for malleable segment 210M depicts sheath 213, malleable wire 230 and wires 232. Sheath 213 made be manufactured from polyolefin (e.g., heat shrink tubing) to protect the cables from damage, such as, for example, fraying, etc. Malleable wire 230 may be manufactured from a malleable metal, such as, for example, aluminum, etc.; in many embodiments, malleable wire 230 weighs about 16 to 18 grams. Wires 232 may be single or multiple strands of copper wire that are clad with high-resistance insulation material, such as, for example, a dielectric material, etc.; certain wires may be unclad. In many embodiments, the wires include a ground wire, a power wire, and two or more signal wires; the signal wires may be untwisted or twisted pairs.

Advantageously, the diameter of the malleable segment 210M is smaller than the diameter of the flexible segment 210F due, at least in part, to the absence of shield 211. In certain embodiments, all of the wires 232 may be twisted together to further reduce the diameter of the malleable segment 210M.

The view of the distal end is a view of the front end of video camera 214 including lens 217. In this embodiment, the light source includes multiple LEDs 219 surrounding lens 217.

Figure 6:
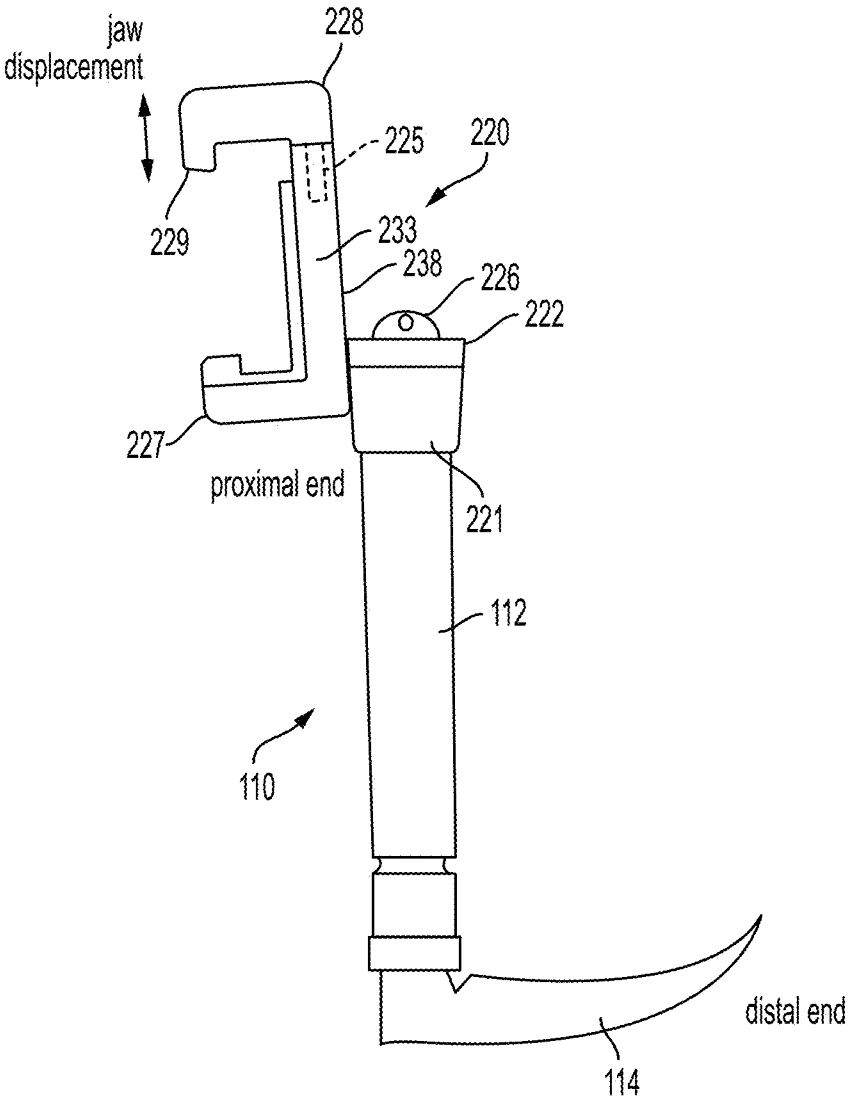
FIG. 6 depicts a laryngoscope and a holder of an LES, in accordance with an embodiment of the present disclosure.
Figure 7A:
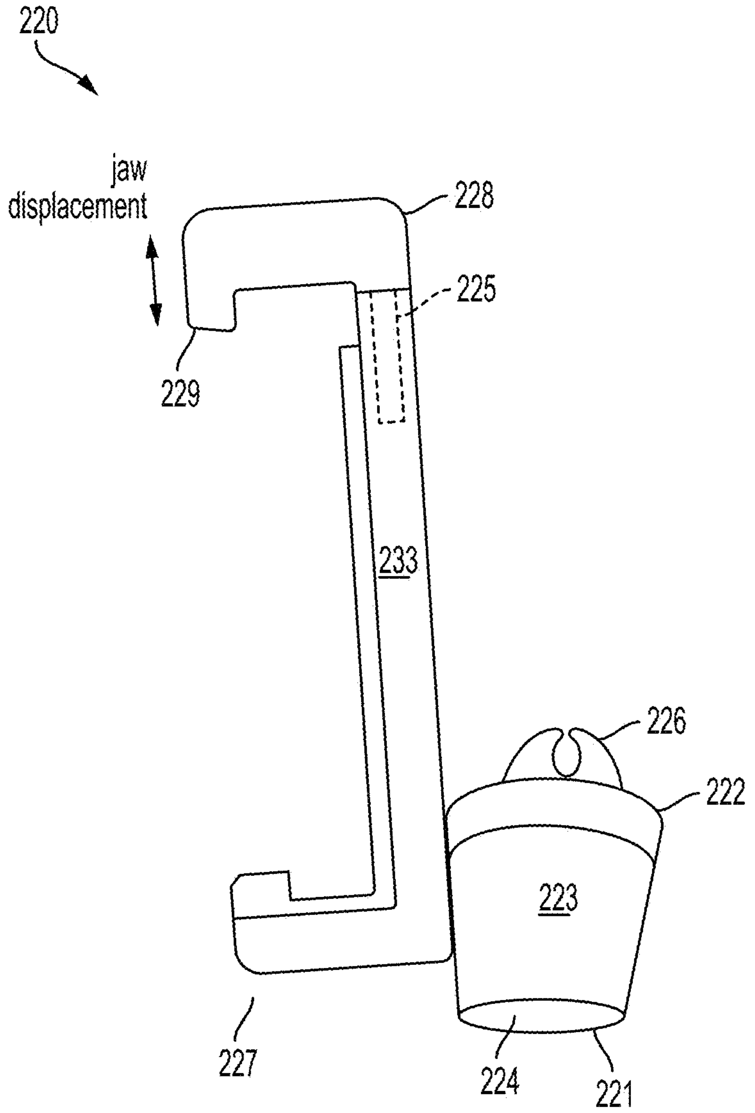
FIGS. 7A, 7B and 7C depict a holder of an LES, in accordance with embodiments of the present disclosure.
Figure 7B:
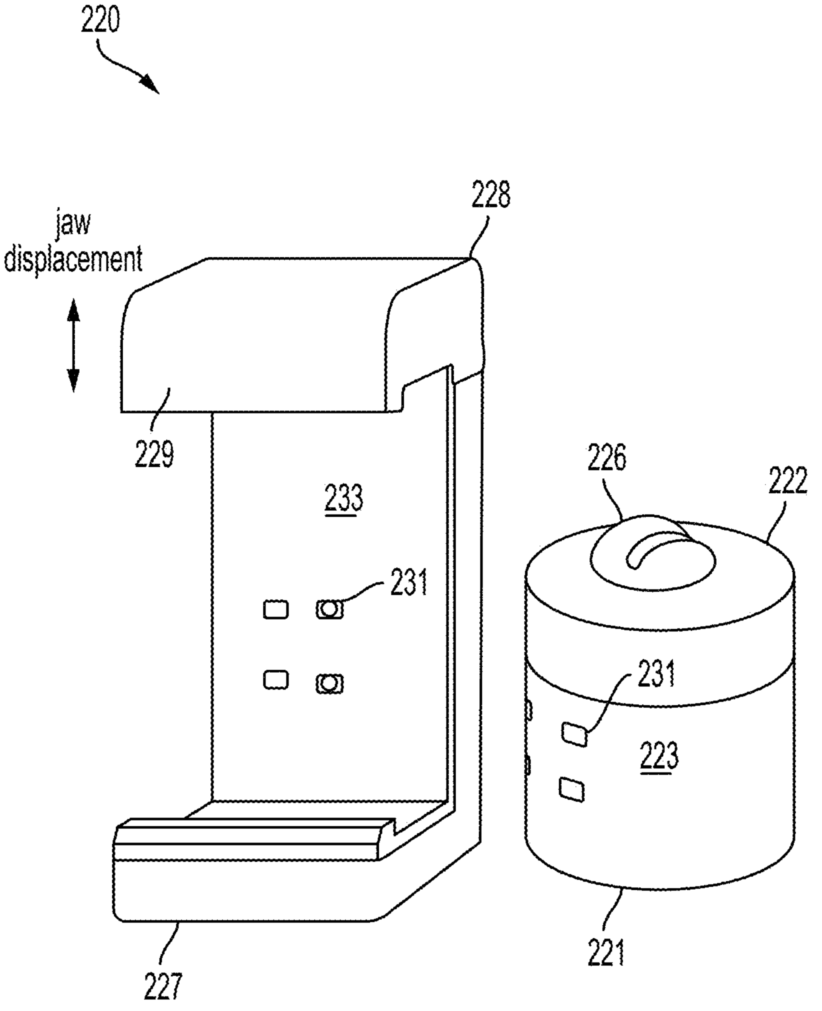
Figure 7C:
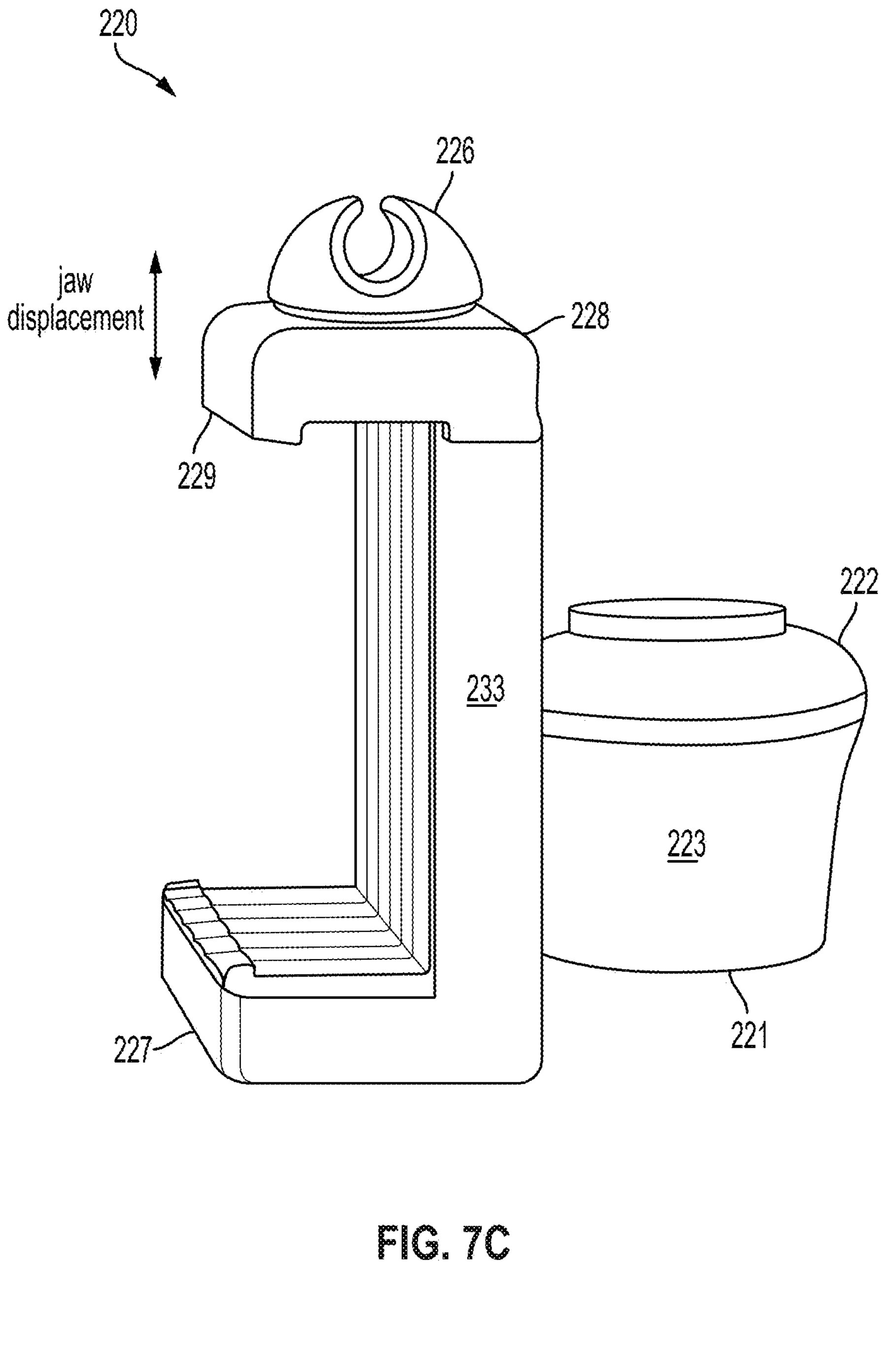
Figure 8A:
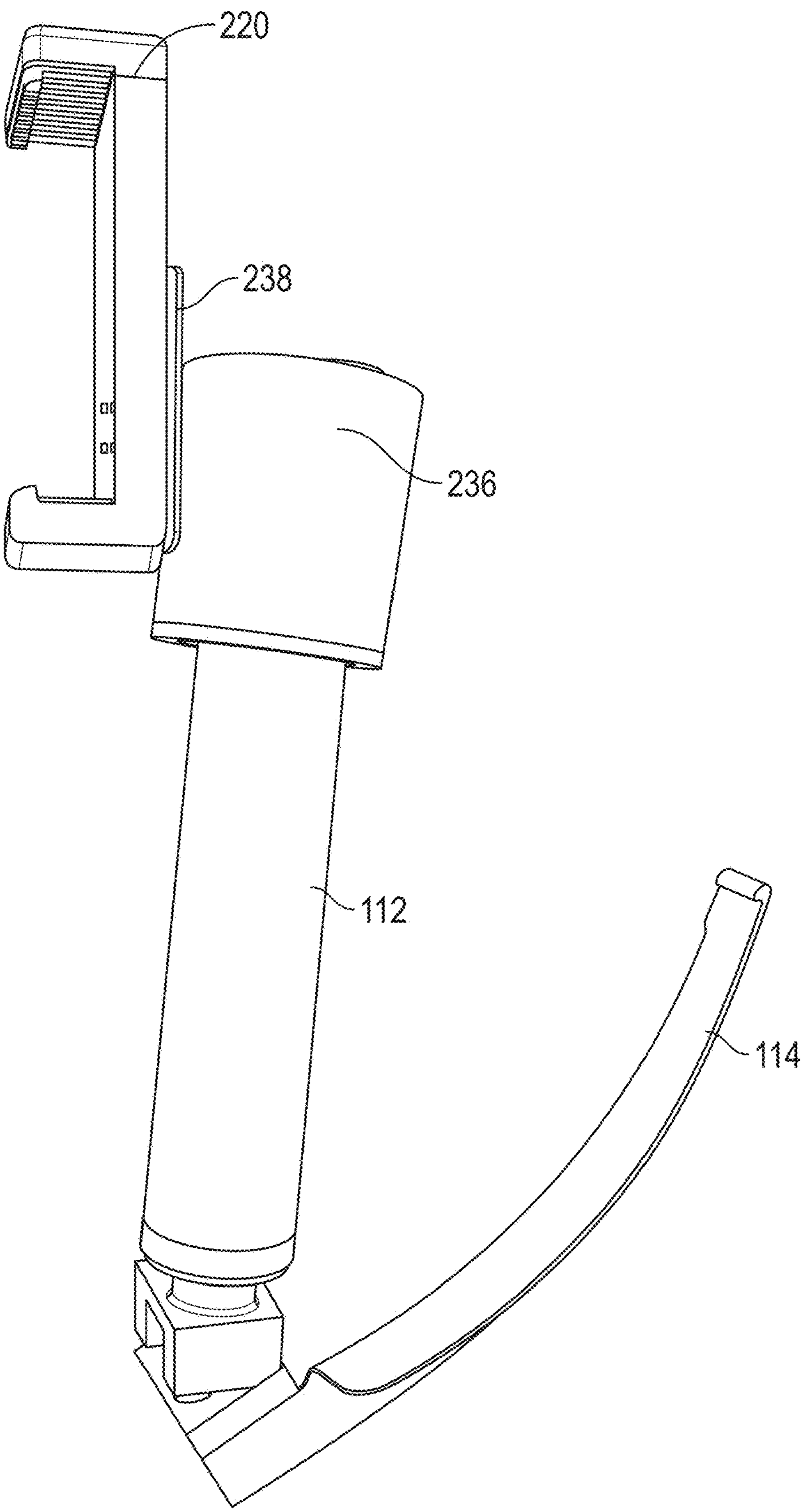
FIGS. 8A, 8B, 8C and 8D depict a shell that covers the end cap or rubber stopper connected to the laryngoscope handle 112, in accordance with embodiments of the present disclosure.
Figure 8B:
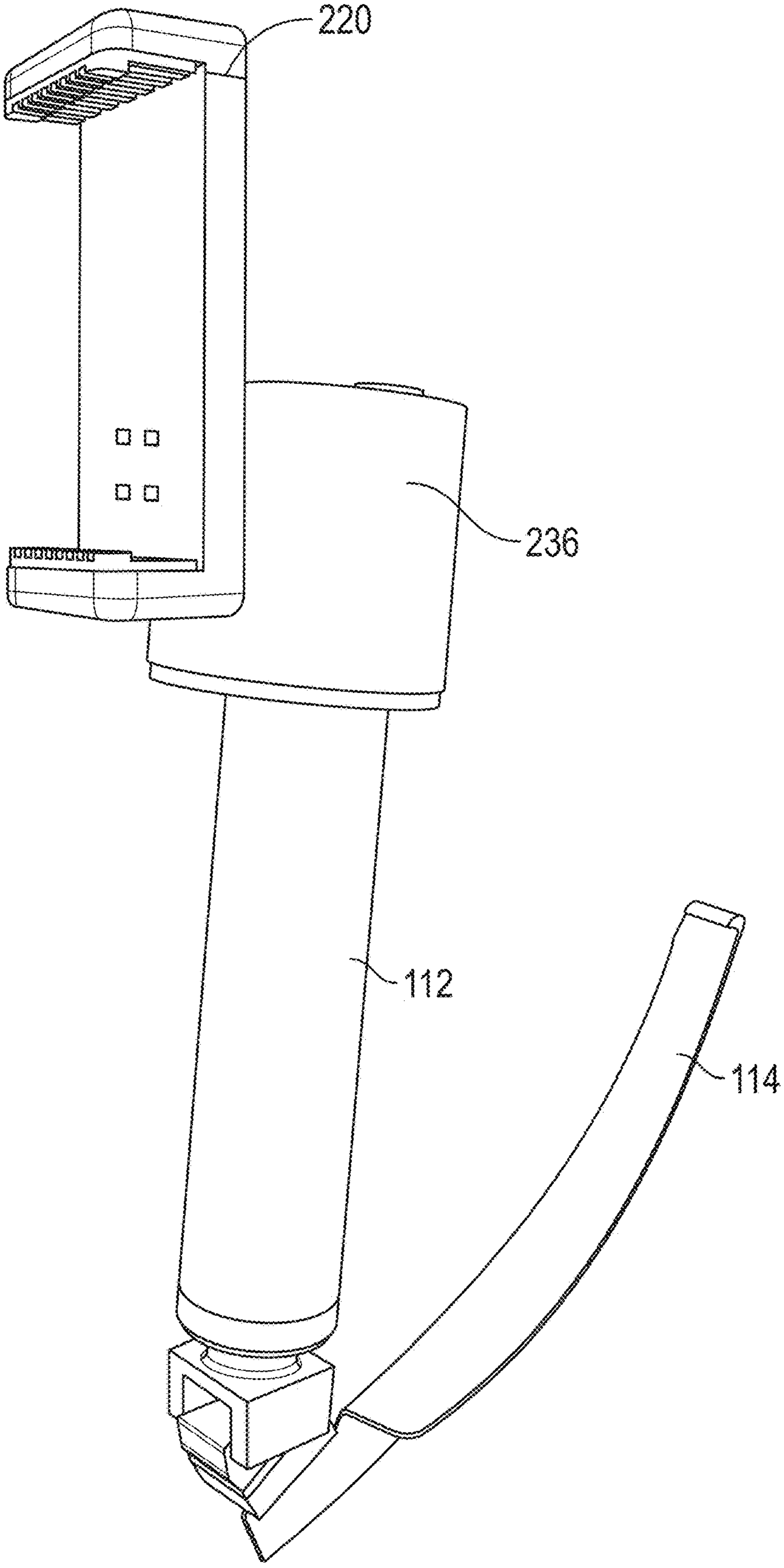
Figure 8C:
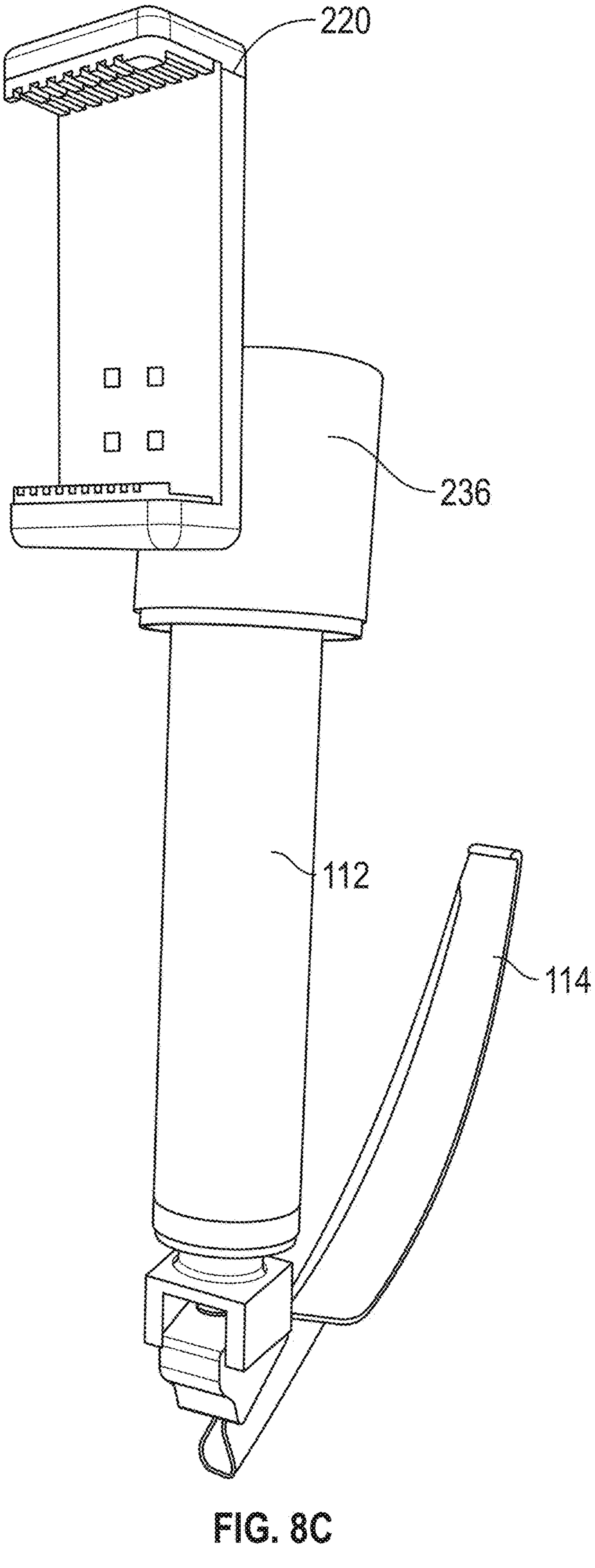
Figure 8D:
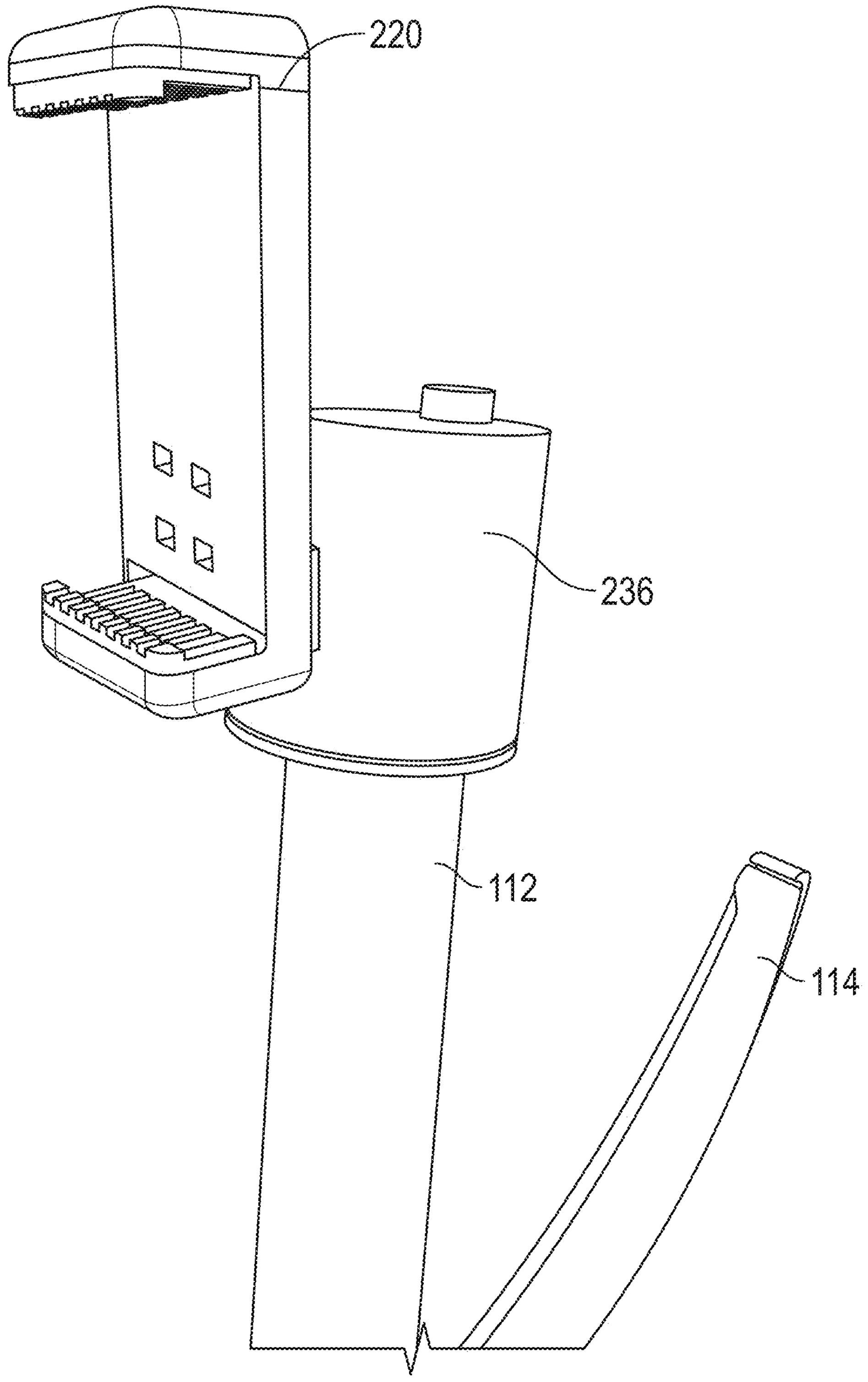

FIG. 6 depicts laryngoscope 110 and holder 220, in accordance with an embodiment of the present disclosure, while FIGS. 7A, 7B and 7C depict holder 220, in accordance with embodiments of the present disclosure.

As described above, laryngoscope 110 includes handle 112, blade 114 and connector 116 that attaches blade 114 to the lower end of handle 112, while holder 220 includes end cap 222 and adjustable mount 228.

End cap 222 is "fixedly" connected to adjustable mount 228. The connection may include glue, epoxy, cable ties, screws, bolts and nuts, rivets, straps, bands, a dovetail connection, and three-dimensional (3-D) connectors, etc. For example, cable ties may be used with co-operating holes 231 in end cap 222 and adjustable mount 228, as depicted in FIG. 7B. End cap 222 has a body 223 that defines a central cavity and lower edge 221 that defines lower opening 224 leading to the central cavity. End cap 222 removably attaches holder 220 to an upper end of handle 112 of laryngoscope 110. Lower opening 224 has a diameter that conforms to the diameter of the upper end of handle 112 of laryngoscope 110, which preferably fills the central cavity when end cap 222 is attached (e.g., 39 mm, etc.). End cap 222 may be manufactured from rubber, plastic, and from 3-D printed material, etc., in various central cavity sizes and lower opening diameters to accommodate different diameter laryngoscope handles.

Adjustable mount 228 releasably secures electronic device 120 to holder 220, and includes fixed jaw 227 and adjustable jaw 229. Positioning device 225, disposed within body 233 of adjustable mount 228, controls the displacement of adjustable jaw 229 along the longitudinal axis of adjustable mount 228. Positioning device 225 may include a spring-loaded ratcheting-type mechanism with a lock button or switch (not shown for clarity) that provides a number of predetermined locked positions or displacements for adjustable jaw 229. Other types of mechanisms are also supported. Adjustable mount 228 may be manufactured from plastic, aluminum, etc., and is sized appropriately to secure electronic device 120 (e.g., 6 inches×3 inches×0.5 inches). For example, the total displacement of adjustable jaw 229 along the longitudinal axis of adjustable mount 228 may be about 4 inches. As indicated in the drawings, body 233 of adjustable mount 228 may have a flat, back surface although other body configurations may be used.

Holder 220 may include guide 226 to support a portion of video stylet 210. In the embodiment depicted in FIG. 6, guide 226 is disposed on an upper portion of end cap 222, while in the embodiment in FIG. 7C, guide 226 is disposed on an upper portion of adjustable mount 228.

The end cap or rubber stopper 222 that connects to the laryngoscope handle 112 may advantageously be covered by a shell, such as a 3-D printed shell 236 as illustrated in FIGS. 8A-8D. The shell 236 may have a flat vertical portion, such as a flat vertical plate, also 3-D printed, that is affixed such as by glue to the flat portion 238 on the back of the holder 220. The flat portion 238 may be an additional surface on the back of the holder 220 as shown or it may be the flat portion of the back of the holder itself, as indicated in other views.

As described herein, a laryngoscope enhancement system is contemplated and envisioned. Such a LES includes a holder, a video stylet, and a wireless adapter. The holder may include a mount configured to releasably secure an electronic device with a display, and an end cap, fixedly connected to the mount, defining a central cavity having a lower opening, the end cap configured to removably attach the holder to an upper end of a laryngoscope handle, the lower opening having a diameter conforming to a diameter of the upper end of the laryngoscope handle. The video stylet may include one or more of a flexible segment including a flexible sheath enclosing a plurality of wires and a malleable segment including a malleable sheath having a smaller diameter than the flexible sheath, and a video camera coupled to one or more of the plurality of wires. The wireless adaptor, coupled to one or more the holder and the video stylet, has a wireless communication capability and an electrical interface configured to communicate with a wireless network interface of a wireless network.

Figure 9:
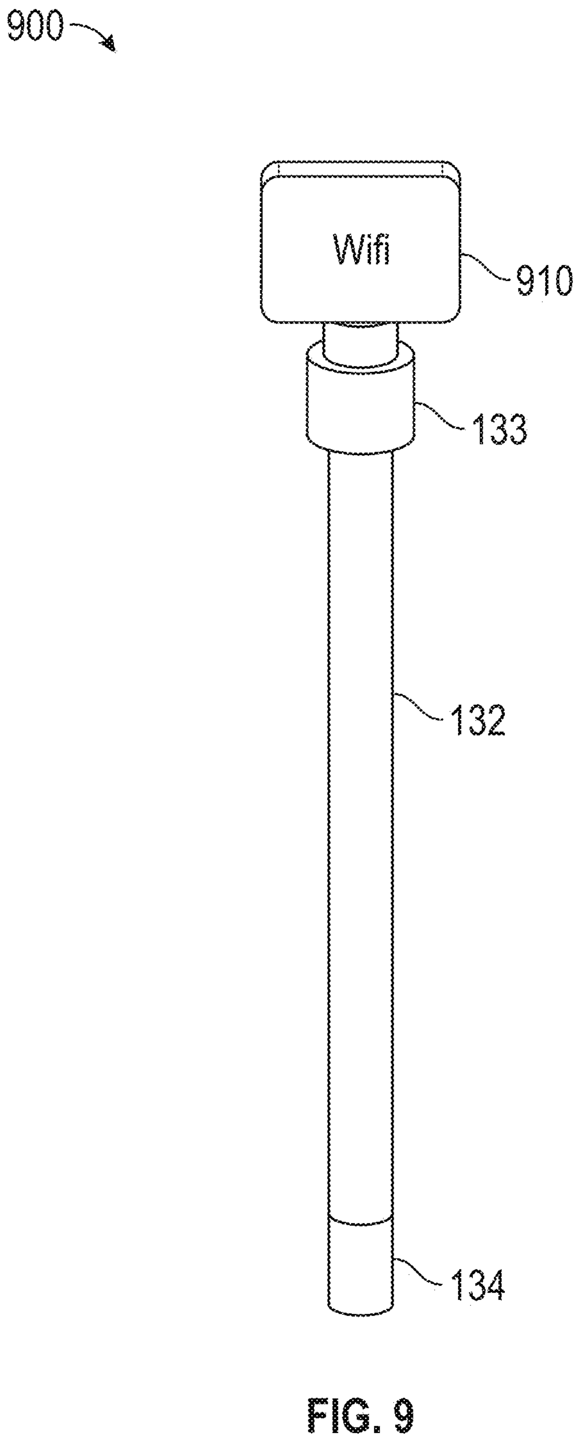
FIG. 9 depicts an endotracheal tube with wireless capability, in accordance with embodiments of the present disclosure.
Figure 10:
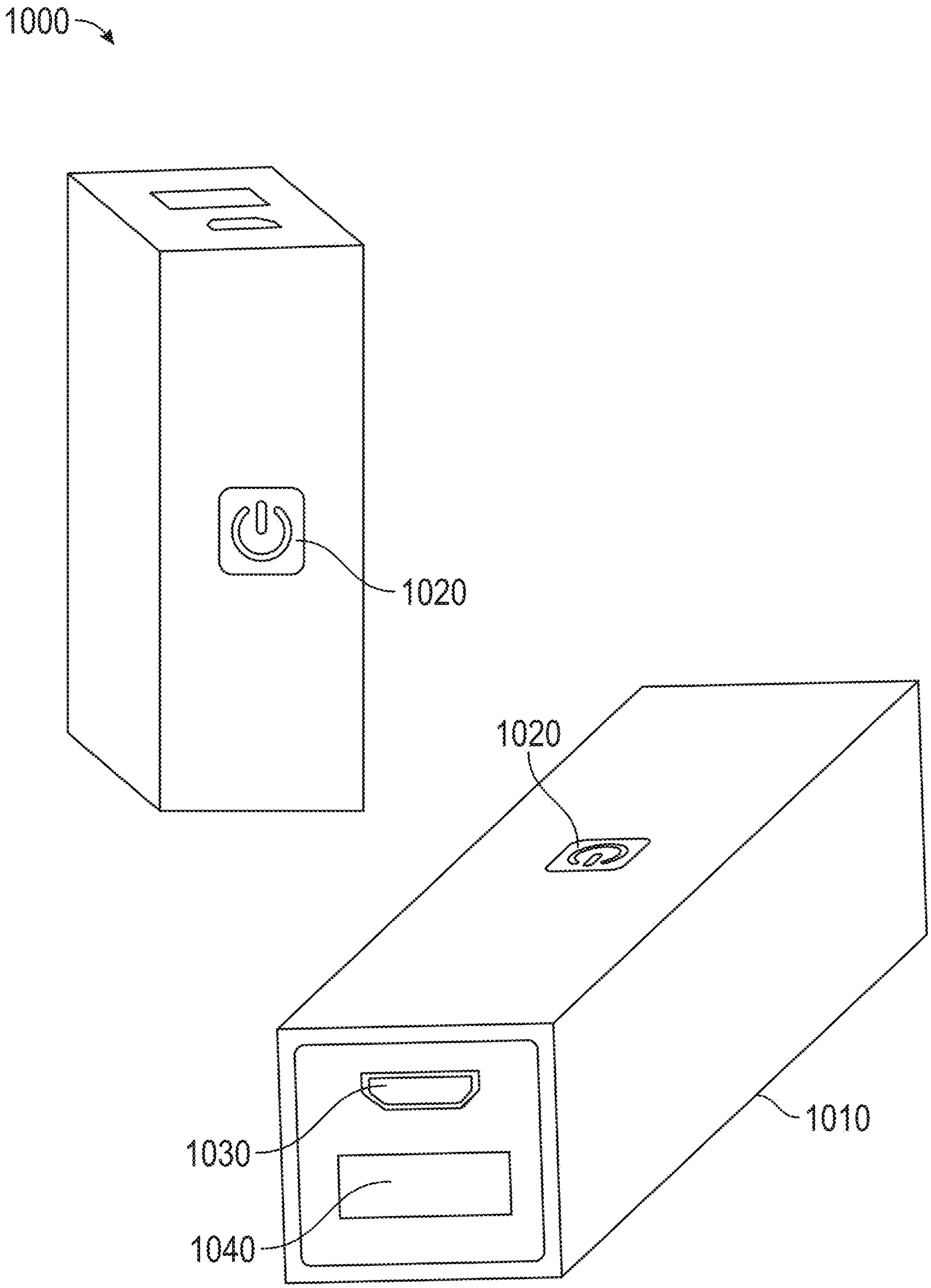
FIGS. 10A, 10B, 10C and 10D show an example wireless adapter having a power one/off button or other control mechanism, as well as a charging port and a USB port, in accordance with embodiments of the present disclosure.

Therefore, as envisioned herein, the ETT 130 may have a distal end 134, which can be beveled, defining a distal opening with a camera, for example. The proximal end 133 of the ETT may have a wireless communication capability, such as provided by a wireless adapter or attachment 910 that supports wireless, Wi-Fi communications, as shown in the wireless ETT 900 in FIG. 9. FIGS. 10A-D show an example wireless adapter 1000 having a power one/off button or other control mechanism 1020, as well as a charging port 1030 for charging and a USB port 1040 for connectivity arranged about a housing 1010 also containing a power source. In certain example embodiments, the wireless adapter 1000 may be a Wi-Fi adapter approximately two inches in length, one inch in width with an internal power source, such as a rechargeable 3.7 V 550 mAh battery or the like inside the adapter housing 1010. The USB-port attachment 1040 provides for device connection that permits wireless (Wi-Fi) video transmission of the video camera 214 tip to a Wi-Fi-connected device. Adjacent the USB port 1040 is a charging port 1030 that allows the adapter battery to be re-charged when not in use. The power on/off button or toggle 1020 is operable to trigger a wireless connection once a device is connected to the USB port. While the wireless adapter 1000 is rectangular in shape, it is contemplated that other arrangements of the ports and the power button and other shapes overall may be employed. Such a housing, illustrated in FIGS. 17A-17D as connector housing 1710, for example, may reside between a device holder and a handle connector.

Figure 11:
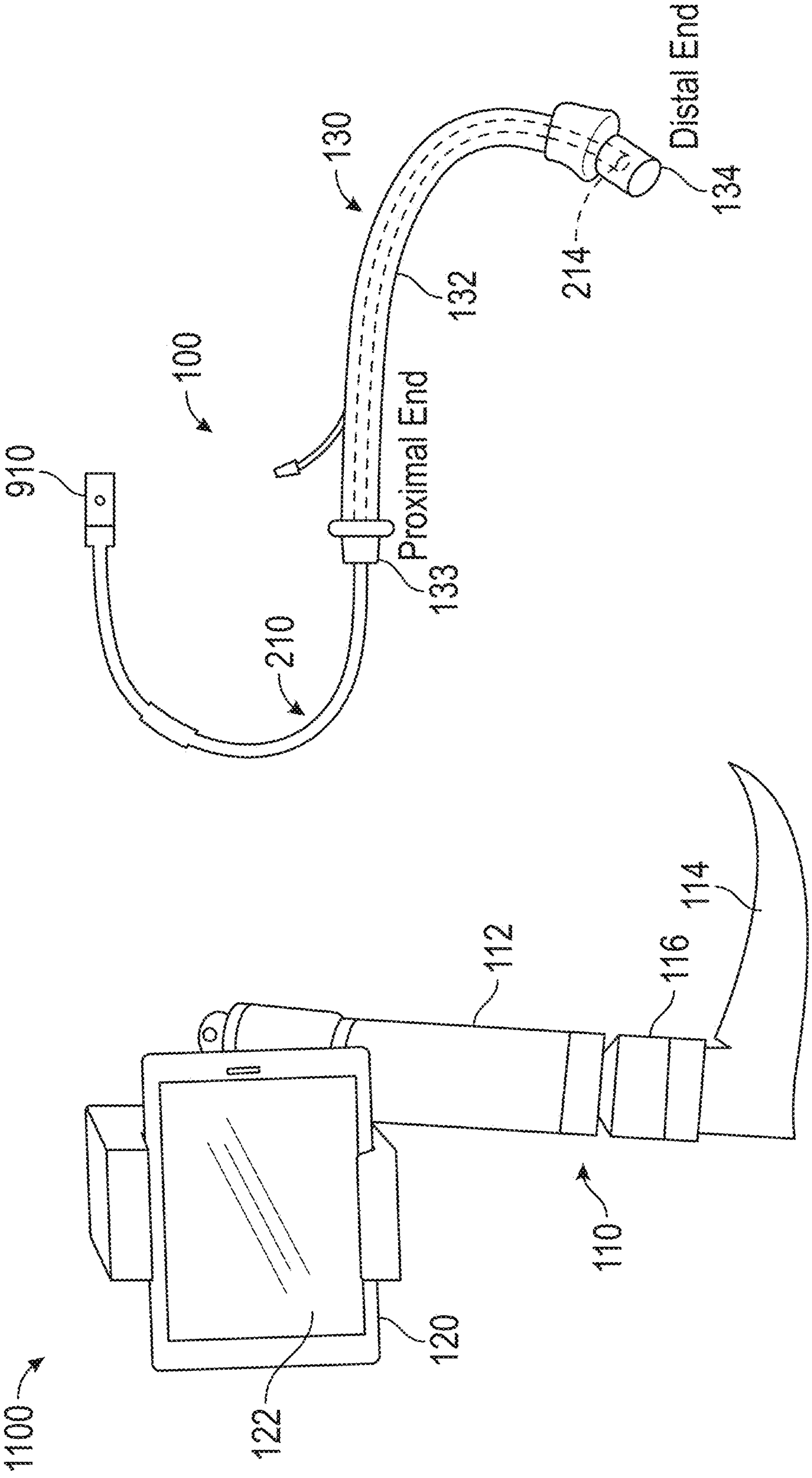
FIG. 11 depicts an intubation system in which an ETT with wireless capability is employed, in accordance with embodiments of the present disclosure.
Figure 12:
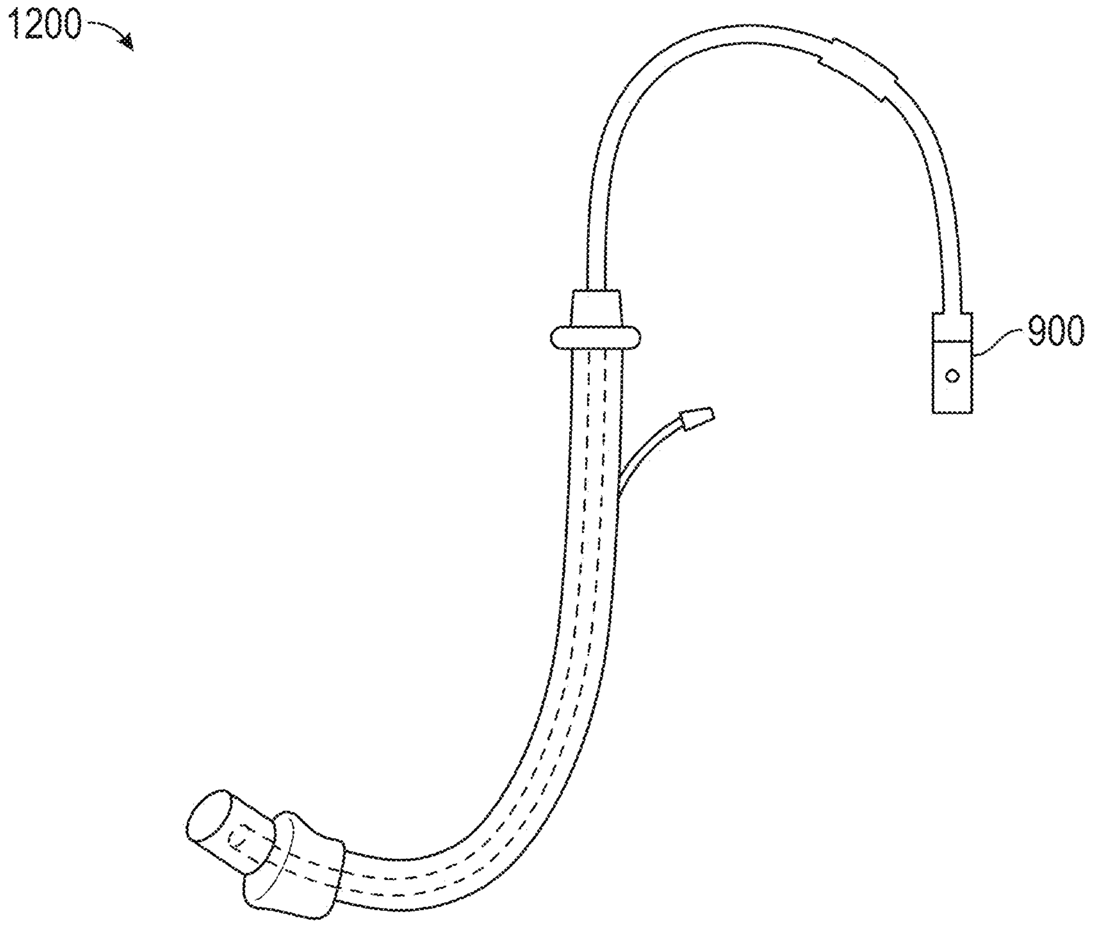
FIG. 12 depicts an ETT with wireless capability, in accordance with embodiments of the present disclosure.
Figure 13:
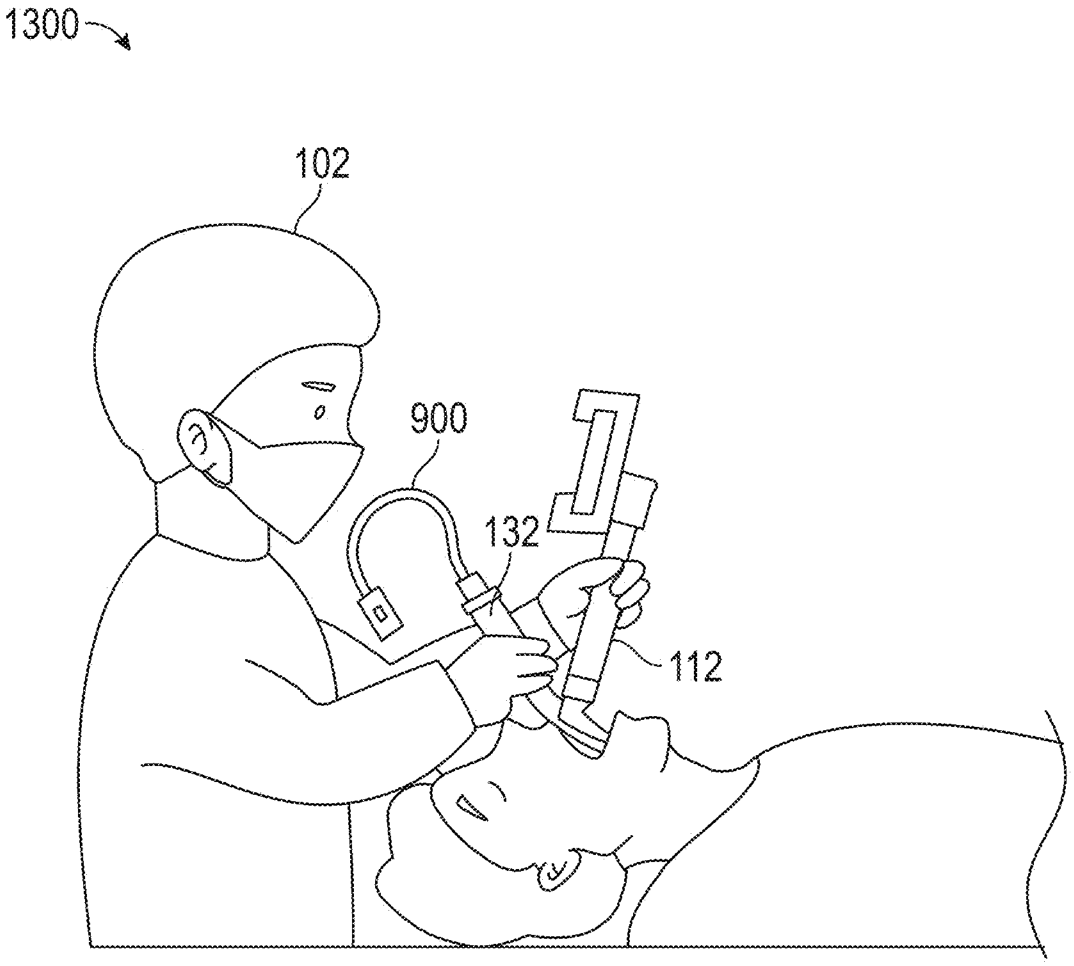
FIG. 13 depicts an in-situ operation 1300 of an IS using a wireless ETT, in accordance with embodiments of the present disclosure.

ETT 900 with wireless capability can be used together with a blade, whether a Macintosh (curved) blade, a Miller (straight) blade, or other blade configurations, or separately. FIG. 11 intubation system (IS) 1100 illustrates an example embodiment in which an ETT with wireless capability 900 is employed. With the wireless arrangement shown, the video stylet 210 need not be physically connected to the electronic device 120, the handle 112 and blade 114. The proximal end 133 of tube 132 is connected to wireless adapter 910 while the distal end 214 of tube 132 has a video camera 134. The proximal end of the ETT is connected to a wireless adapter 910, such as via a USB port, for example. In this example arrangement, the ETT no longer needs to be connected via a wired connection directly to the visual display screen 122 of the device 120. The visual display screen 122 wirelessly connects to ETT 900 via the wireless adapter 910 to receive and display video and images captured by the camera at the distal end. IS 1200 of FIG. 12 shows a similar configuration for a wireless ETT 900. FIG. 13 depicts in-situ operation 1300 of an IS using a wireless ETT, in accordance with an embodiment of the present disclosure. It can be seen that a healthcare provider 102 holds handle 112 of laryngoscope 110 in one hand and tube 132 of wireless ETT 900 in the other hand. Thus, the decoupled relationship between the handle and the wireless ETT, in which independent movement and use of the handle and the wireless ETT, is shown and contemplated, in accordance with certain embodiments.

It can therefore be appreciated that an intubation system having an endotracheal tube having an inner diameter; an electronic device with a display; and a laryngoscope is described, with the laryngoscope having a blade, a handle, connected to the blade, having an upper end and a diameter, and a holder. The holder includes a mount configured to releasably secure the electronic device with a display, an end cap, fixedly connected to the mount, defining a central cavity having a lower opening, the end cap configured to removably attach the holder to an upper end of a laryngoscope handle, the lower opening having a diameter conforming to a diameter of the upper end of the laryngoscope handle; a video stylet, including: one or more of a flexible segment including a flexible sheath enclosing a plurality of wires and a malleable segment including a malleable sheath having a smaller diameter than the flexible sheath, and a video camera coupled to one or more of the plurality of wires; and a wireless adaptor, coupled to one or more the holder and the video stylet, having a wireless communication capability and an electrical interface configured to communicate with a wireless network interface of a wireless network.

In addition to the separate arrangement of a wireless ETT from the blade and handle of a laryngoscope system, the arrangement of a wireless capability and a video camera with attendant light source within or integral to the blade portion is additionally contemplated. In such embodiments, the wireless ETT may be realized as a borescope imbedded into a 3-D printed intubation blade, for example.

Accordingly, there is contemplated and envisioned a laryngoscope with a handle portion, a blade portion coupled to the handle portion, a video stylet embedded within one or more of the handle portion and the blade portion; and a wireless adapter coupled to the video stylet having a wireless communication capability and an electrical interface configured to communicate with a wireless network interface of a wireless network.

Figure 14B:
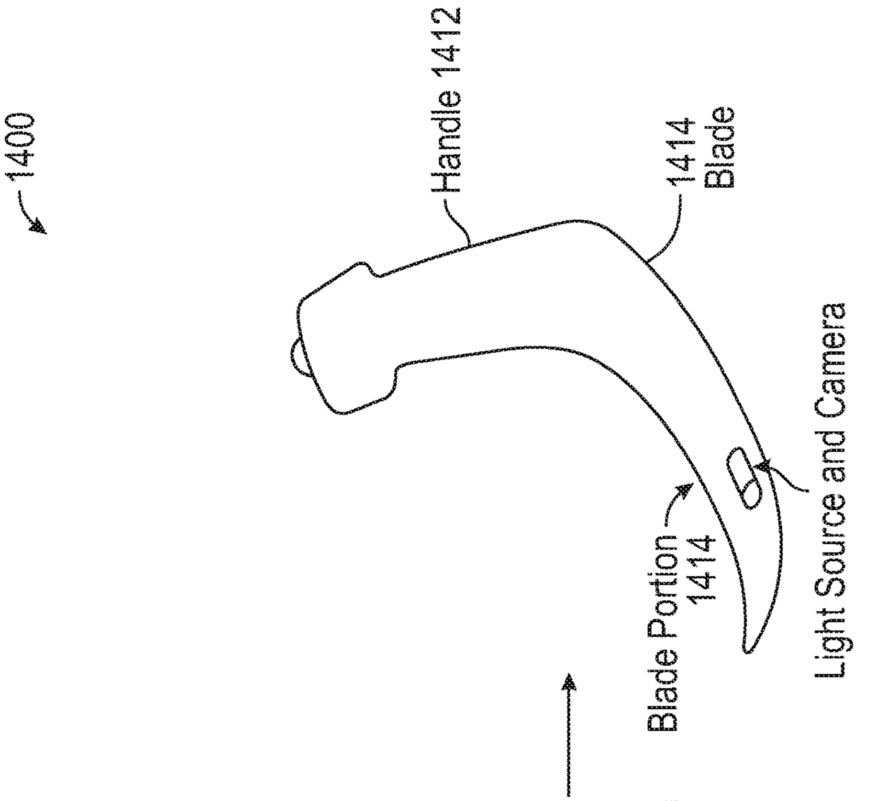
FIGS. 14A and 14B show a laryngoscope blade 1400 with wireless capability and a curved blade configuration, in accordance with embodiments of the present disclosure.
Figure 14A:
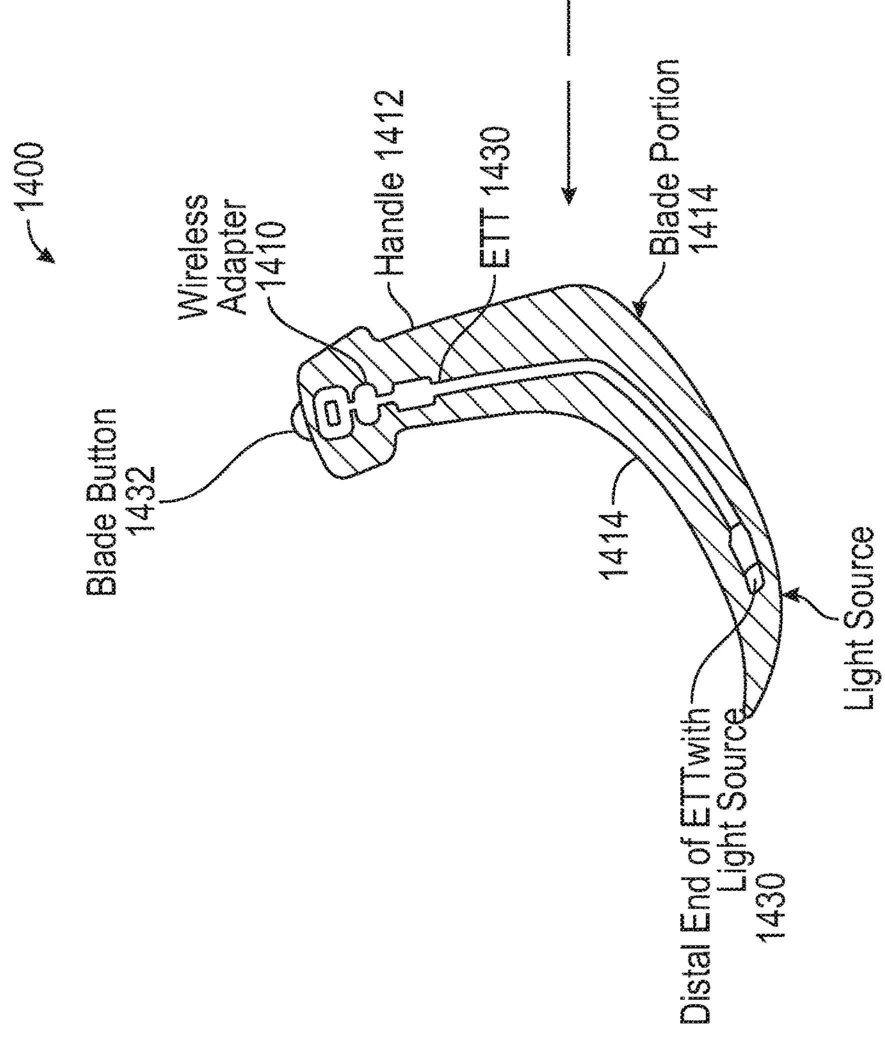
Figures 15A, 15B:
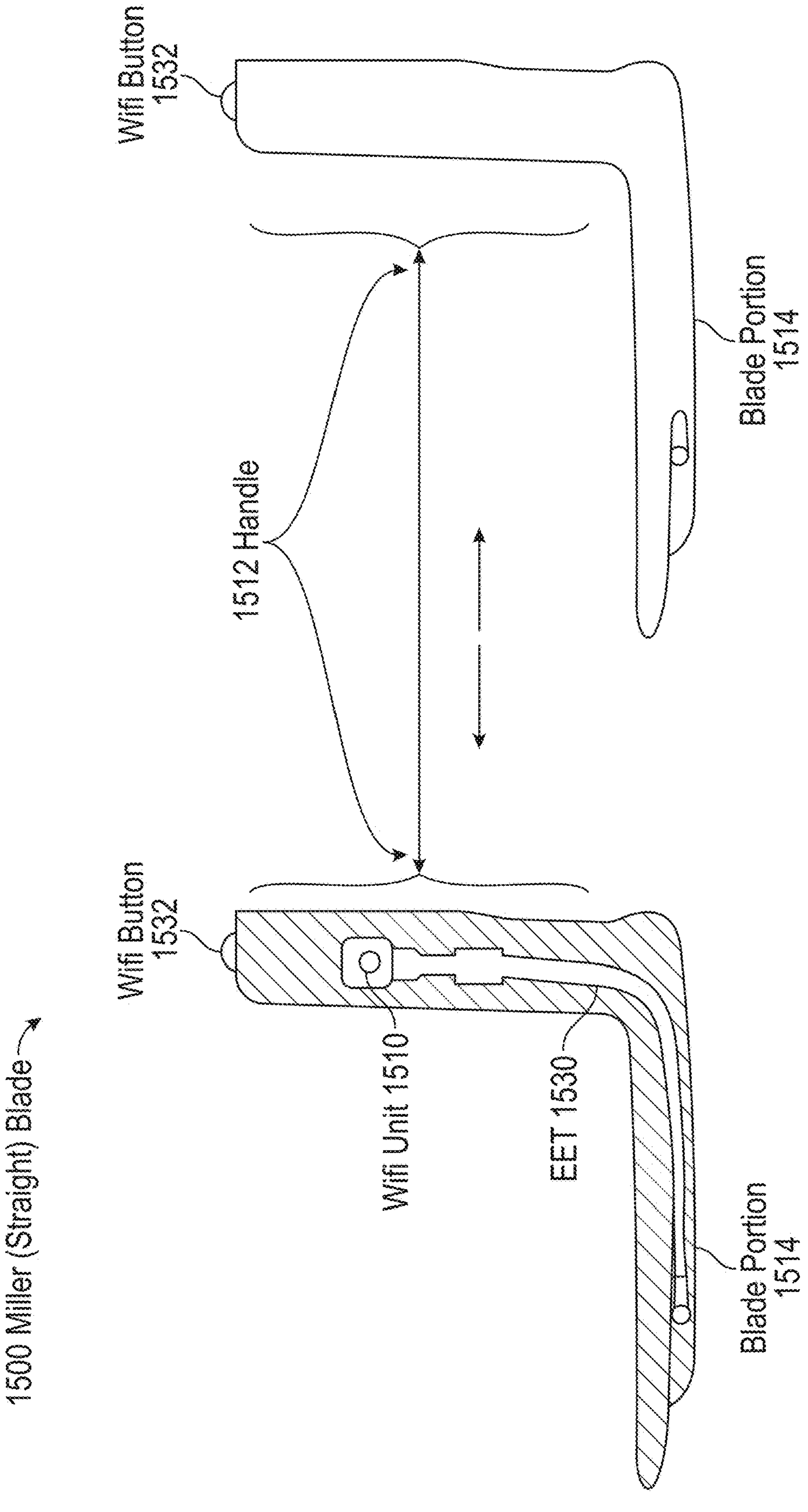
FIGS. 15A and 15B show a laryngoscope blade 1400 with wireless capability and a straight blade configuration, in accordance with embodiments of the present disclosure.

Referring now to FIGS. 14A and 14B, a laryngoscope blade 1400 with wireless capability is depicted. Wireless blade 1400 is shown as a Macintosh (curve) blade, although other configurations, such as a Miller (straight) blade in FIGS. 15A and 15B, are contemplated. Wireless blade 1400 has a blade portion 1414 and a handle portion 1412 in which ETT 1430 with wireless capabilities is embedded within the laryngoscope blade 1400 as indicated in the cross-sectional view of FIG. 14A. The distal end of ETT 1430 has a light source with a camera near the tip of the blade, while the proximate end of ETT 1430 has a wireless adapter 1410, the power button of which is accessible to the healthcare provider. It is understood that variations in embodiments include the blade portion 1414 alone or the blade with the handle portion 1412, all as one unit, as shown in the drawing.

In the embodiment of FIGS. 14A and 14B in which the blade and handle portions together form a single wireless blade 1400, the device, whether it be a smart phone or other device capable of fitting within the blade, is embedded inside the blade with the tip of the device serving as both a light source and camera of the laryngoscope blade 1400. Inside the blade portion 1414 is contained the proximal end of the device with a small wireless (Wi-Fi) unit connected. The top portion of the handle may contain a Wi-Fi power button 1432 connected to the device as shown.

Referring now to FIGS. 15A and 15B, examples of a laryngoscope blade 1500 having an embedded wireless capability is depicted.

Wireless blade 1500 is shown as a Miller (straight) blade, although other configurations, such as a Macintosh (curve) blade in FIGS. 14A and B, are contemplated. Wireless blade 1500 has a blade portion 1514 and a handle portion 1512 in which ETT 1530 with wireless capabilities is embedded within the laryngoscope blade 1500 as indicated in the cross-sectional view of FIG. 15A. The distal end of ETT 1530 has a light source with a camera near the tip of the blade, while the proximate end of ETT 1530 has a wireless adapter 1510, the power button 1532 of which is accessible to the healthcare provider. It is understood that variations in embodiments include the blade portion 1514 alone or the blade with the handle portion 1512, all as one unit, as shown in the drawing.

In the embodiment of FIGS. 15A and 15B in which the blade and handle portions together form a single wireless blade 1500, the device, whether it be a smart phone or other device capable of fitting within the blade, is embedded inside the blade with the tip of the device serving as both a light source and camera of the laryngoscope blade 1500. Inside the blade portion 1514 is contained the proximal end of the device with a small wireless (Wi-Fi) unit connected. The top portion of the handle may contain a Wi-Fi power button 1532 connected to the device as shown.

Figures 16A, 16B:
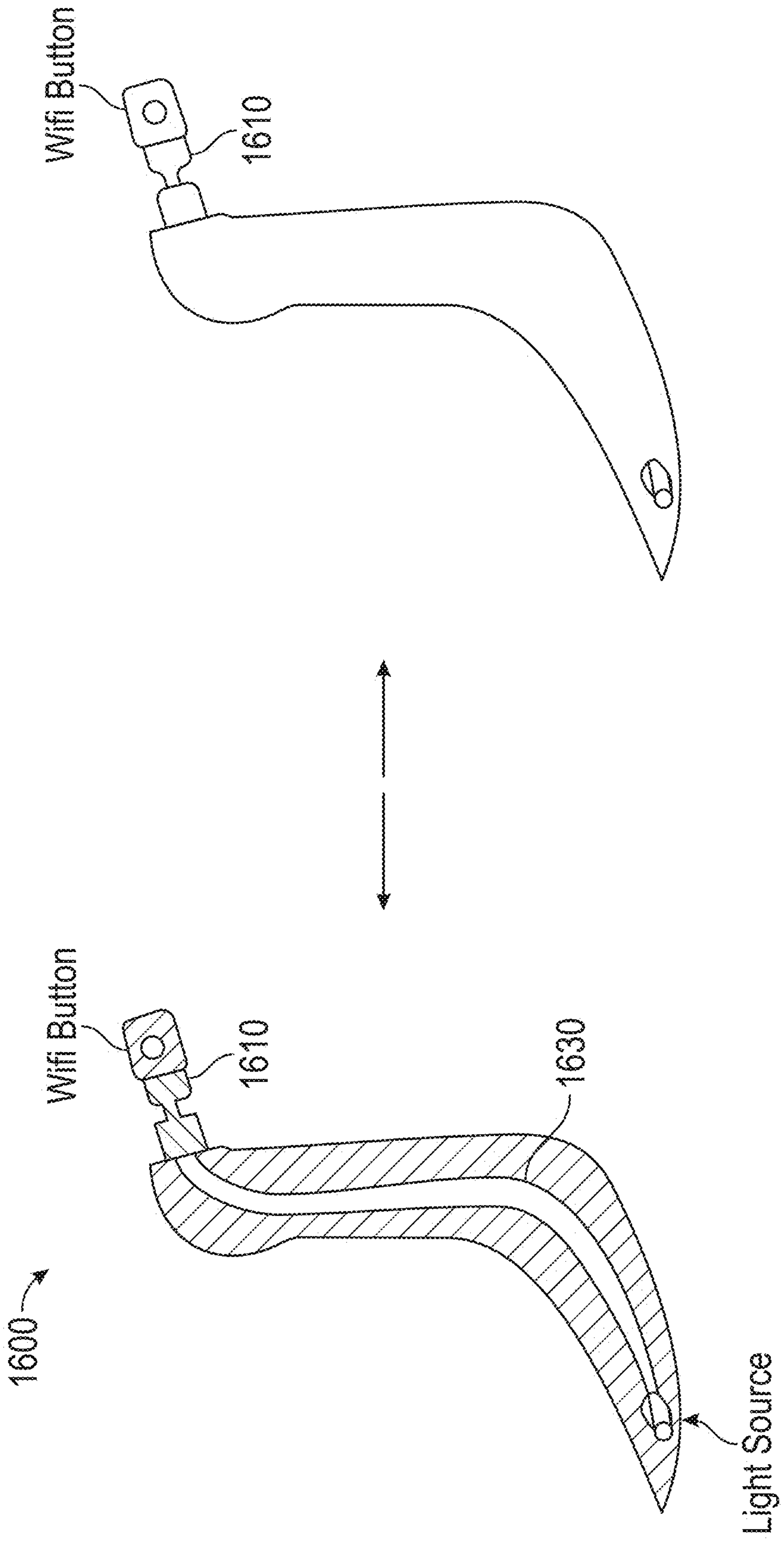
FIGS. 16A and 16B depict an ETT with wireless capabilities, embedded within a variation laryngoscope, in accordance with embodiments of the present disclosure.
Figure 17A:
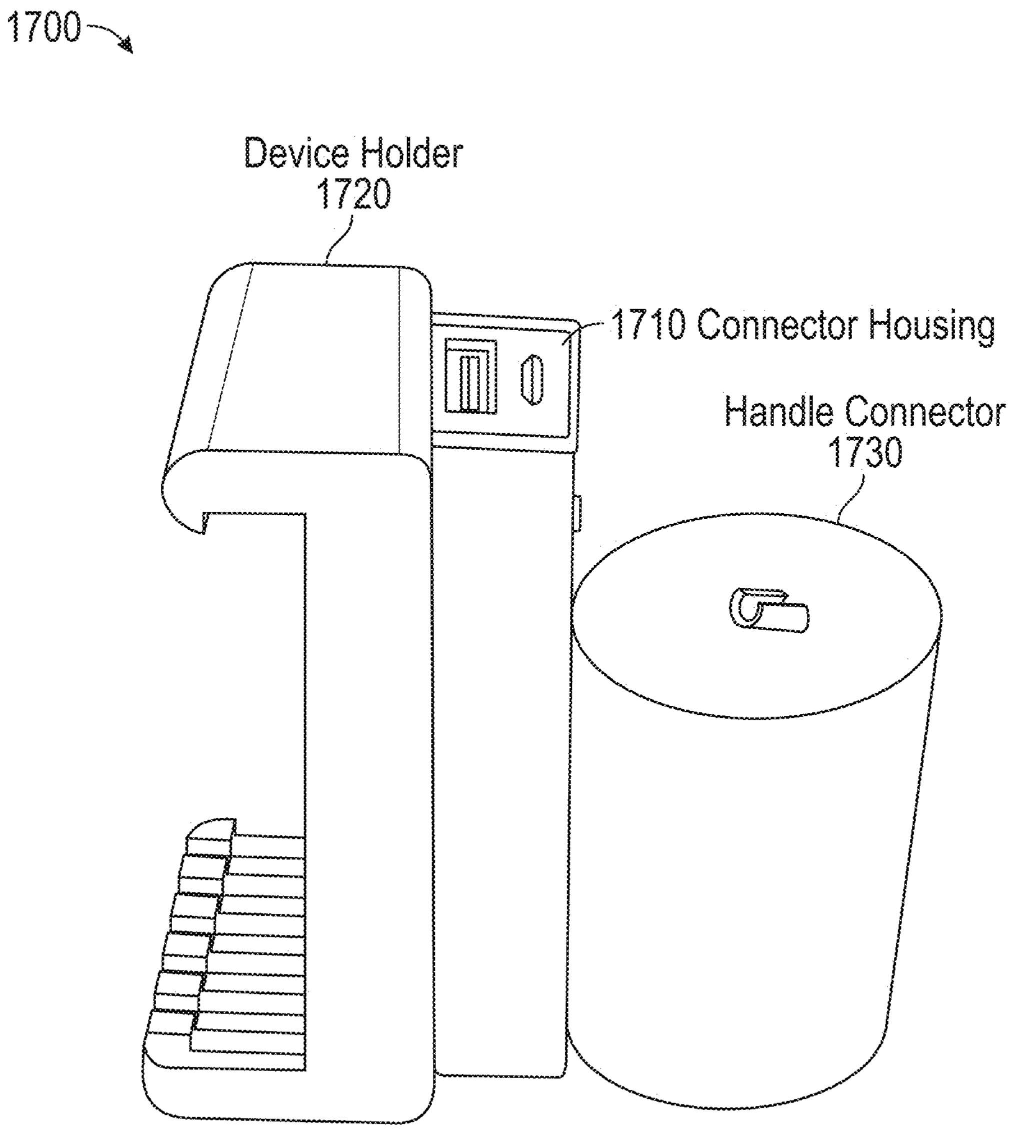
FIGS. 17A, 17B, 17C and 17D depict a connector having wireless capabilities of an LES having wireless capabilities, in accordance with further embodiments of the present disclosure.
Figure 17B:
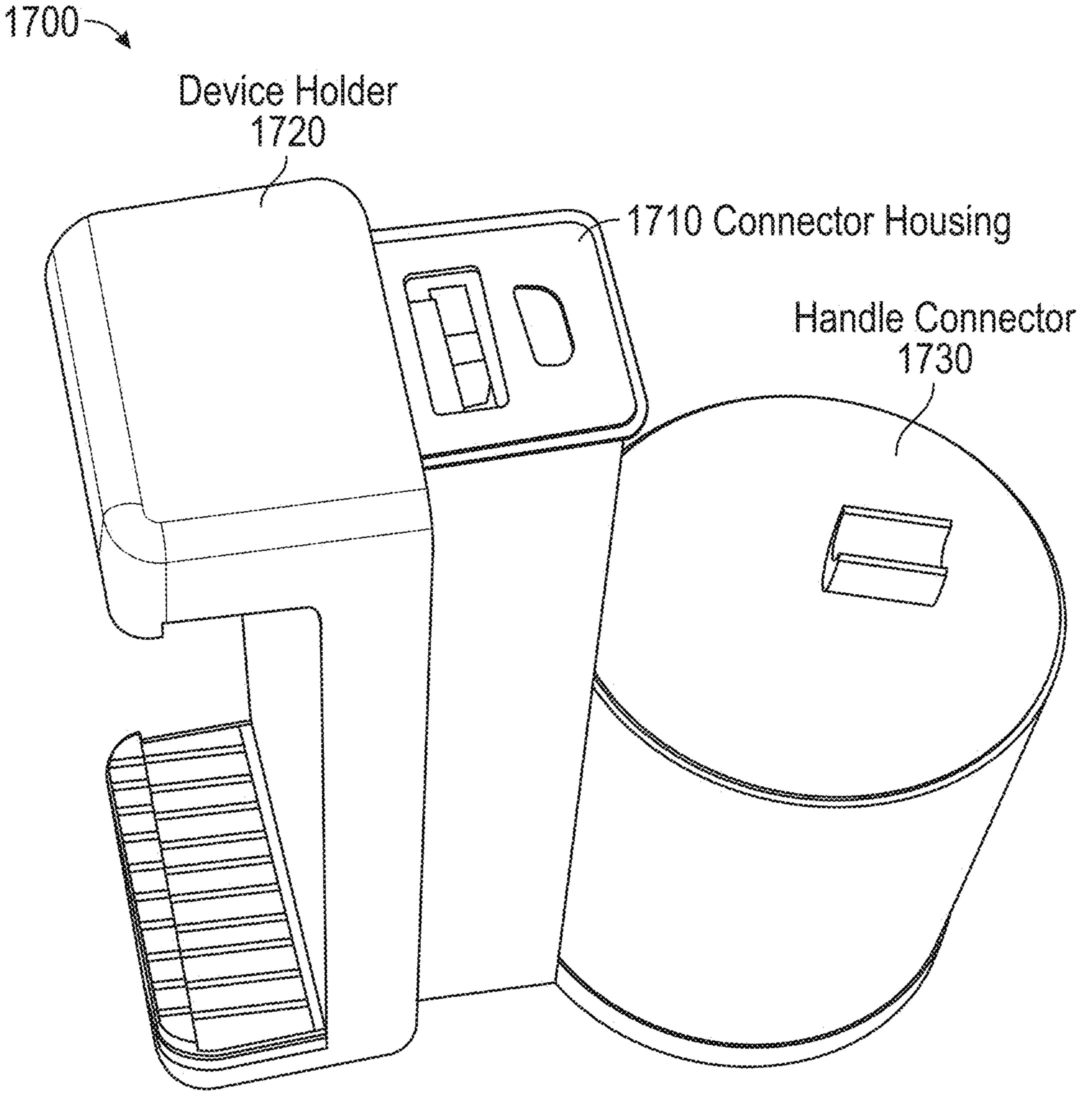
Figure 17C:
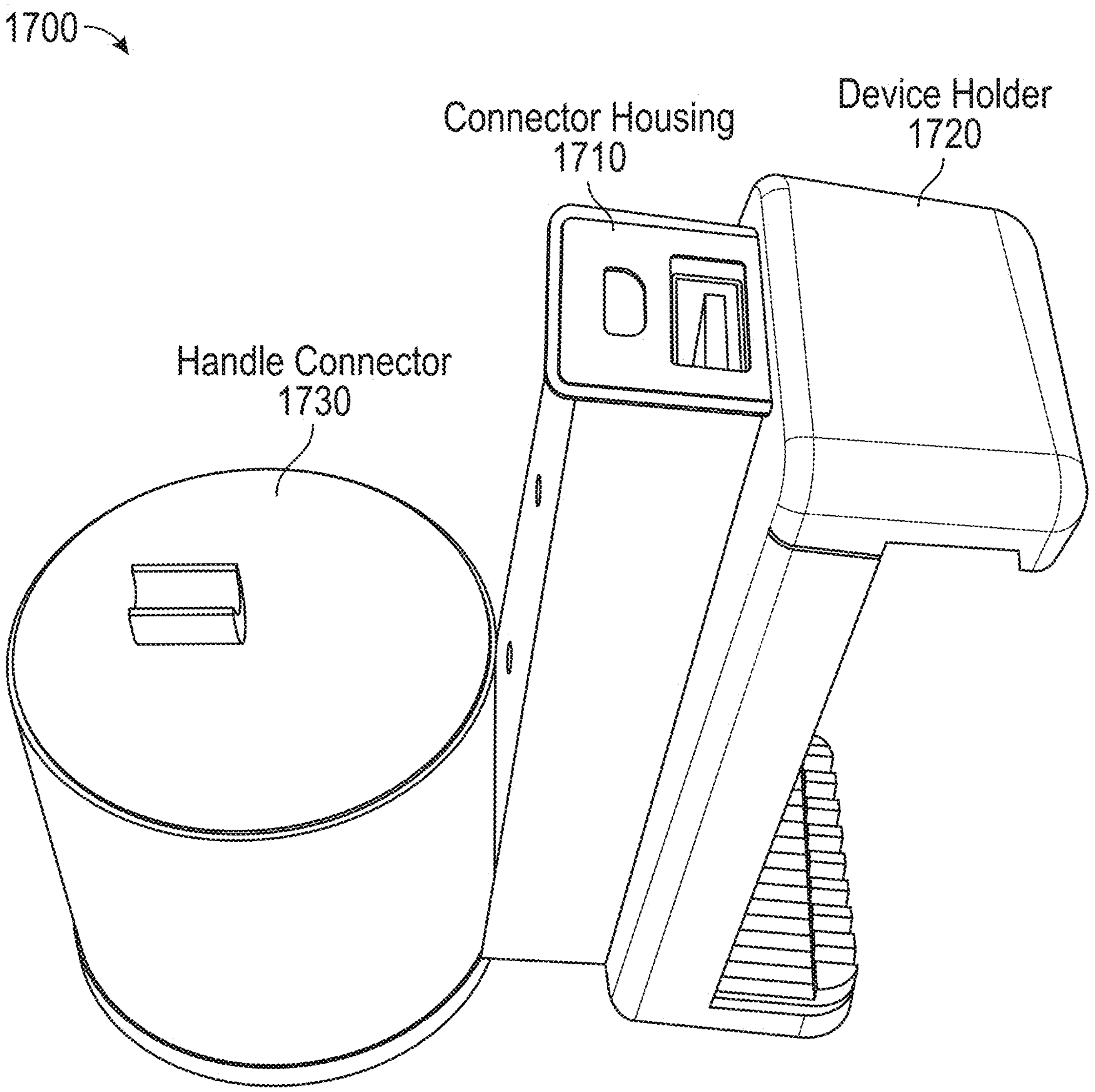
Figure 17D:
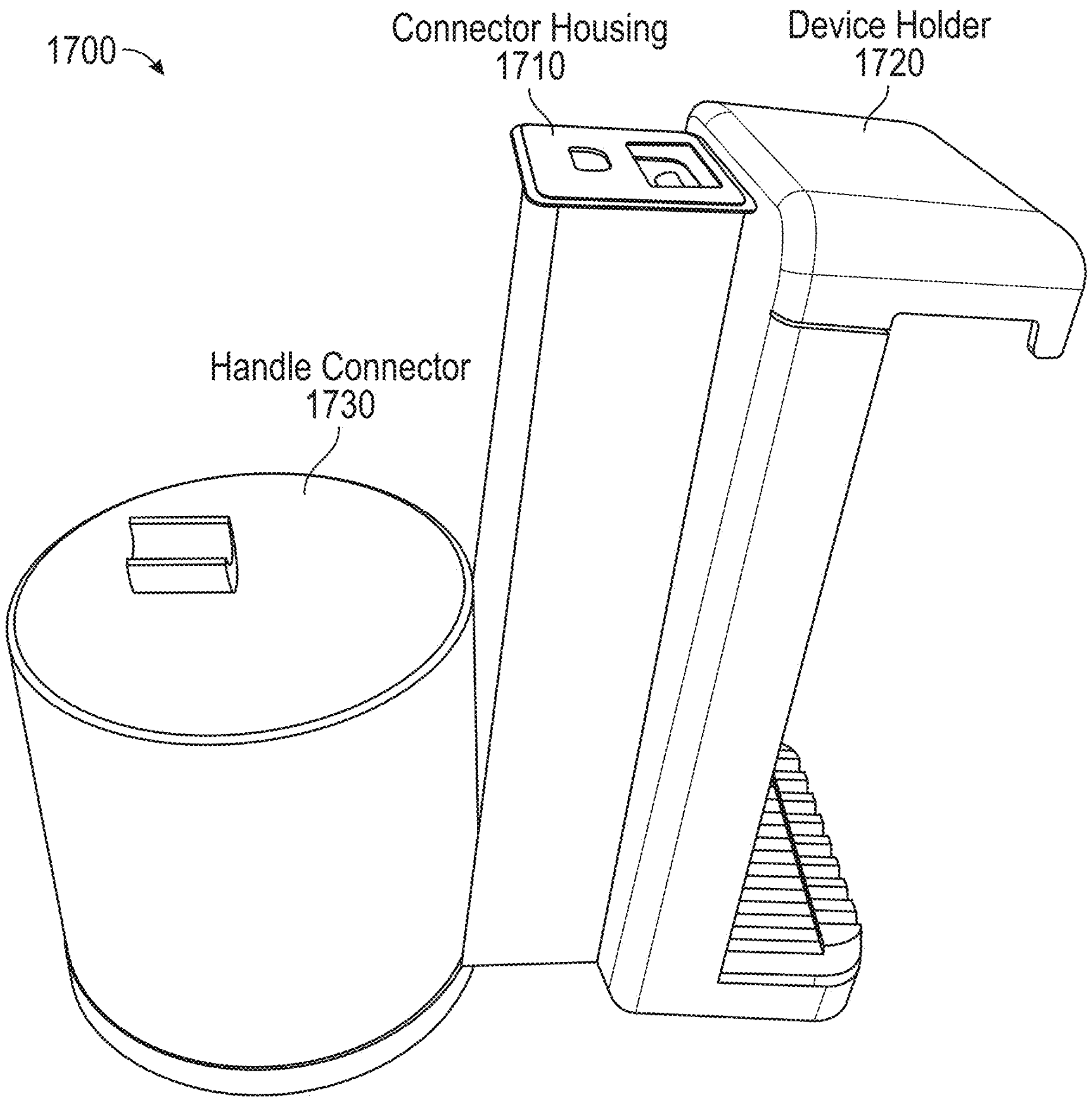

Referring now to FIGS. 16A and 16B, an embodiment in which an ETT 1630 with wireless capabilities is embedded within a variation laryngoscope 1600 is depicted. Unlike the embodiments of FIGS. 14A, 14B, 15A, 15B, the shape of the laryngoscope is referred to as a variation laryngoscope in which the blade and handle portions blend together as integrated parts. In this particular example, the wireless adapter Wi-Fi unit 1610 protrudes outside the handle portion of the top.

Referring now to FIGS. 17A to 17D, various views of a connector having wireless capabilities is depicted. In these drawings, the Wi-Fi portions are housed in a connector housing 1710 in-between the device holder 1720 and the handle connector 1730. This preserves the circular nature of the handle connector. Rather than the USB port being imbedded in the circular portion of the holder, such as shown in FIG. 18B, the USB port resides in a substantially flat, rectangular connector housing in-between the device holder and the handle connector as shown.

It can be seen from the above description, endotracheal intubation using wireless technology to place breathing tubes into the airway of a patient is envisioned.

Figure 18A:
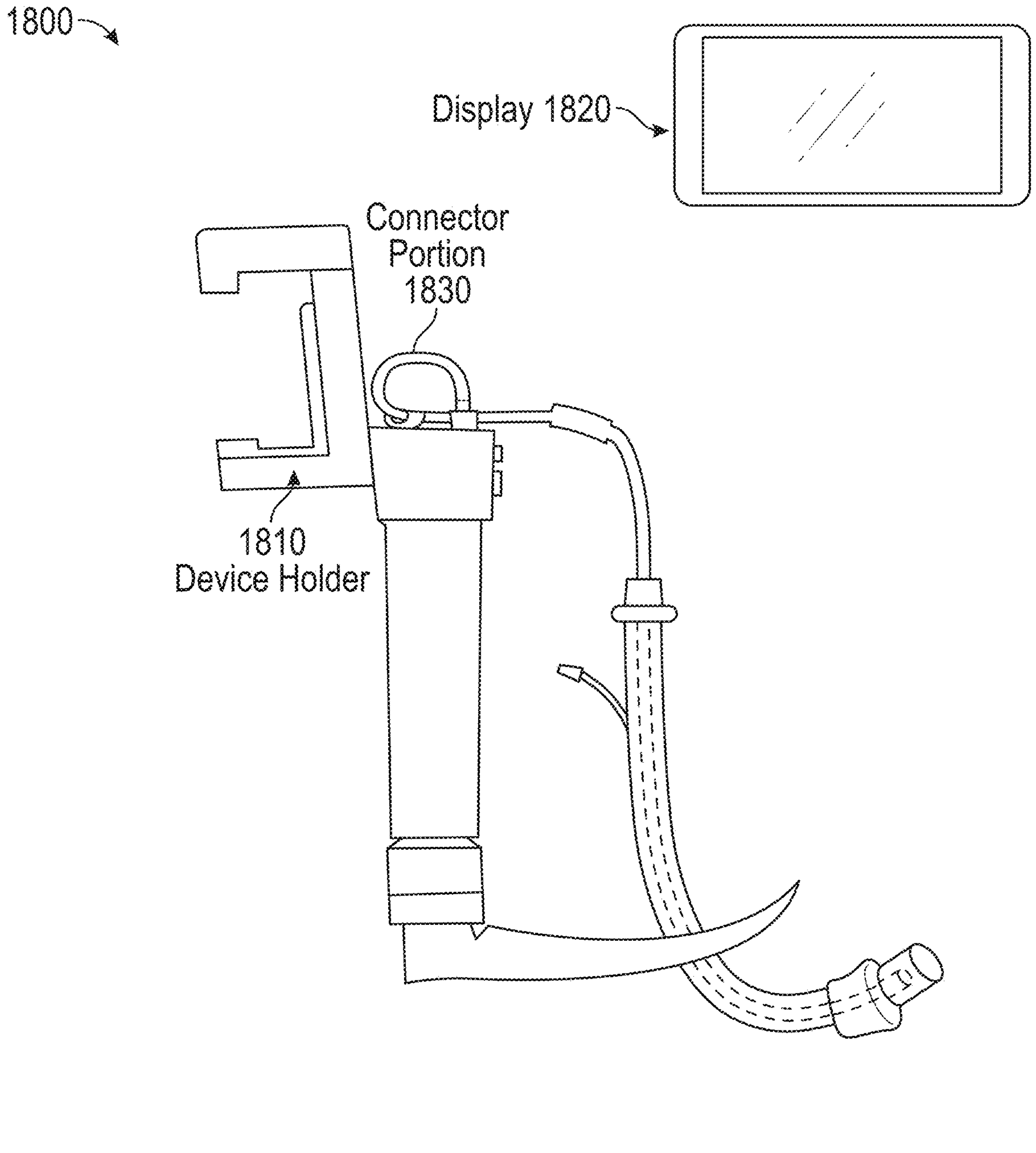
FIGS. 18A, 18B and 18C depict a wireless capability imbedded inside a device or display holder, in accordance with further embodiments of the present disclosure.
Figure 18B:
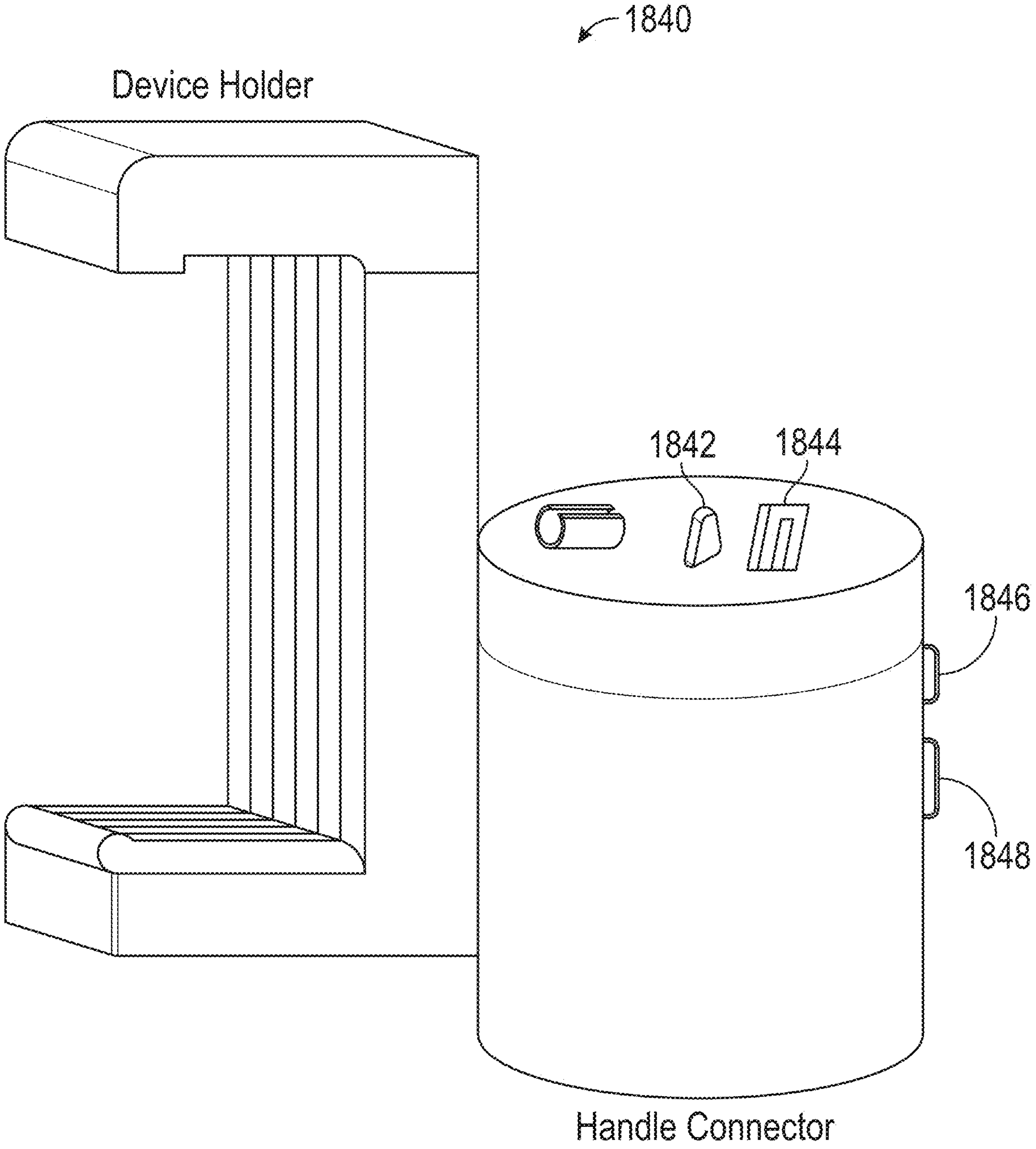
Figure 18C:
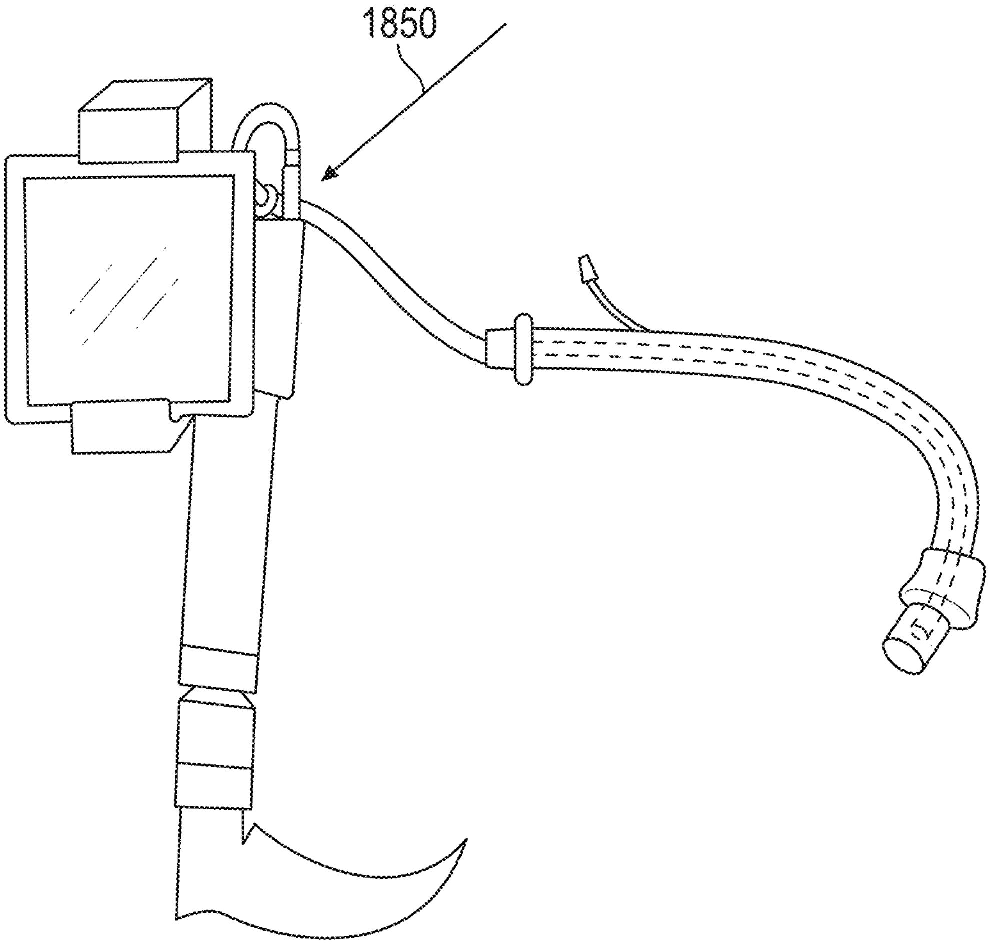

Referring now to FIGS. 18A-18C, various embodiments in which a wireless capability is imbedded inside a device or display holder is shown. In FIG. 18A, a wireless adapter is imbedded inside the display holder 1810. The proximal end of the ETT is connects to a wireless adapter via a USB port imbedded inside the display holder 1810. In this option, the ETT need no longer needs to be connected via wire directly to visual display screen but rather to the display holder. The visual display screen 1820 wirelessly connects to the ETT via Wi-Fi adapter video and images. As shown in FIGS. 18A and 18B, on the connector portion 1830 of the display holder 1810 are four 4 features: a USB connection for the proximal end of invention connection; a charger connection to recharge the rechargeable battery embedded in connector; a charge light indicator to indicate charting status of connector, and a power switch to turn on the wireless connection. As seen in the examples shown in FIGS. 18A and 18C, images are displayed to screen wirelessly with no requirement to holster display screen to display holder 1810 and there is no requirement for direct wired connection of the ETT to a display screen.

In FIG. 18B a detailed rendering of a display holder 1840 with charging port 1842, USB port 1844 for ETT connection, charging indicator 1846, and power switch button 1848 for wireless connection activation, all within a display holder connector portion, is shown. Inside the display holder connector portion may be a rechargeable 3.7 V 550 mAh battery or similar. The connection afforded by display holder 1840 would permit Wi-Fi video transmission of images/video from a camera tip to the Wi-Fi-connected device. Immediately adjacent to USB port 1844 charging port 1842 allows the Wi-Fi-adapter battery to be recharged when not in use. On the rear side portion of handle connector portion a power on/off button 1846 may be used to trigger a Wi-Fi connection once a device received by display holder 1840 is connected to USB port 1844.

In FIG. 18C, it is illustrated that images may be displayed to a screen wirelessly 1850 while the display screen is optionally holstered to display holder. Again, there is no requirement for direct wired connection of the ETT to a display screen.

It can therefore be appreciated that an intubation system having an endotracheal tube having an inner diameter; an electronic device with a display; and a laryngoscope is described, with the laryngoscope having a blade, a handle, connected to the blade, having an upper end and a diameter, and a holder. The holder includes a mount configured to releasably secure the electronic device with a display, an end cap, fixedly connected to the mount, defining a central cavity having a lower opening, the end cap configured to removably attach the holder to an upper end of a laryngoscope handle, the lower opening having a diameter conforming to a diameter of the upper end of the laryngoscope handle; a video stylet, including: one or more of a flexible segment including a flexible sheath enclosing a plurality of wires and a malleable segment including a malleable sheath having a smaller diameter than the flexible sheath, and a video camera coupled to one or more of the plurality of wires; and a wireless adaptor, coupled to one or more the holder and the video stylet, having a wireless communication capability and an electrical interface configured to communicate with a wireless network interface of a wireless network.

The following embodiments are combinable.

In one embodiment, a laryngoscope enhancement system includes: a holder having a mount configured to releasably secure an electronic device with a display and an end cap, fixedly connected to the mount, defining a central cavity having a lower opening, the end cap configured to removably attach the holder to an upper end of a laryngoscope handle, the lower opening having a diameter conforming to a diameter of the upper end of the laryngoscope handle; and a video stylet, including: a plurality of wires, a connecter, coupled to the plurality of wires, removably attachable to an electronic device, the connector having built-in Wi-Fi capacity for wireless connection; an additional connector, coupled to the plurality of wires, having an electrical interface configured to communicate with a wireless network interface of a wireless network; a flexible segment including a flexible sheath enclosing the plurality of wires, a malleable segment including a malleable sheath enclosing a malleable wire and the plurality of wires, the malleable sheath having a smaller diameter than the flexible sheath, and a video camera coupled to one or more of the plurality of wires.

In another embodiment of the laryngoscope enhancement system, the additional connector has a different electrical interface than the connector.

In another embodiment of the laryngoscope enhancement system, the additional connector is removably connectable to an additional electronic device.

In another embodiment of the laryngoscope enhancement system, the electronic device is a smart phone and the additional electronic device is a display.

In another embodiment of the laryngoscope enhancement system, the video stylet includes a light source coupled to at least one of the plurality of wires, and the flexible segment includes a light source control unit coupled to the at least one of the plurality of wires.

In another embodiment of the laryngoscope enhancement system, the light source includes a plurality of light emitting diodes that surround a lens of the video camera.

In another embodiment of the laryngoscope enhancement system, the additional connector is configured to communicate with one or more of a Wi-Fi network interface of the electronic device and a Wi-Fi network interface of an additional electronic device.

In one embodiment, an intubation system includes: an endotracheal tube having an inner diameter; an electronic device with a display; and a laryngoscope. The laryngoscope includes: a blade; a handle connected to the blade, having an upper end and a diameter; a holder, including a mount releasably securing the electronic device; and an end cap defining a central cavity having a lower opening, the end cap removably attached to the upper end of the handle, the lower opening having a diameter conforming to the diameter of the handle, and a video stylet, including: a plurality of wires, a connecter, coupled to the plurality of wires, removably attachable to the electronic device, the connector having built-in Wi-Fi capacity for wireless connection; an additional connector, coupled to the plurality of wires, having an electrical interface configured to communicate with a wireless network interface of a wireless network, a flexible segment including a flexible sheath enclosing the plurality of wires, a malleable segment including a malleable sheath enclosing a malleable wire and the plurality of wires, the malleable sheath having a smaller diameter than the flexible sheath, and a video camera coupled to one or more of the plurality of wires.

In another embodiment of the intubation system, the additional connector has a different electrical interface than the connector.

In another embodiment of the intubation system, the additional connector is removably connectable to an additional electronic device.

In another embodiment of the intubation system, the electronic device is a smart phone and the additional electronic device is a display.

In another embodiment of the intubation system, the video stylet includes a light source coupled to at least one of the plurality of wires, and the flexible segment includes a light source control unit coupled to the at least one of the plurality of wires.

In another embodiment of the intubation system, the additional connector is configured to communicate with one or more of a Wi-Fi network interface of the electronic device and a Wi-Fi network interface of an additional electronic device.

In one embodiment, a laryngoscope enhancement system includes a holder; a video stylet; and a wireless adaptor. The holder includes a mount configured to releasably secure an electronic device with a display, and an end cap, fixedly connected to the mount, defining a central cavity having a lower opening, the end cap configured to removably attach the holder to an upper end of a laryngoscope handle, the lower opening having a diameter conforming to a diameter of the upper end of the laryngoscope handle. The video stylet includes: one or more of a flexible segment including a flexible sheath enclosing a plurality of wires and a malleable segment including a malleable sheath having a smaller diameter than the flexible sheath, and a video camera coupled to one or more of the plurality of wires. The wireless adaptor, coupled to one or more the holder and the video stylet, having a wireless communication capability and an electrical interface configured to communicate with a wireless network interface of a wireless network.

In another embodiment of the laryngoscope enhancement system, the holder further including a shell configured to cover the end cap and coupled to the adjustable mount.

In another embodiment of the laryngoscope enhancement system, the shell is configured to couple to a back side of the adjustable mount.

In another embodiment of the laryngoscope enhancement system, a wireless adaptor of the holder having a wireless communication capability and an electrical interface configured to communicate with a wireless network interface of a wireless network.

In another embodiment of the laryngoscope enhancement system, the wireless adaptor of the holder is coupled to one or more of the mount and the end cap of the holder.

In another embodiment of the laryngoscope enhancement system, the wireless adaptor resides between and is coupled to the mount and the end cap of the holder.

In another embodiment of the laryngoscope enhancement system, the wireless adaptor of the holder is integrated in one or more of the mount and the end cap.

In another embodiment of the laryngoscope enhancement system, a wireless adaptor of the video stylet having a wireless communication capability and an electrical interface configured to communicate with a wireless network interface of a wireless network, the wireless adaptor of the video stylet coupled to one or more of the flexible segment, the malleable segment and the video camera.

In another embodiment of the laryngoscope enhancement system, the wireless adaptor of the video stylet is coupled to the camera at a distal end of video stylet.

In another embodiment of the laryngoscope enhancement system, the holder and the video stylet are decoupled with a holder wireless adaptor of the holder in wireless communication with a video stylet wireless adaptor of the video outlet, the holder wireless adaptor configured to couple to a mounted electronic device with a display mounted in the mount.

In one embodiment, an intubation system includes: an endotracheal tube having an inner diameter; an electronic device with a display; and a laryngoscope. The laryngoscope includes a blade, a handle, connected to the blade, having an upper end and a diameter, a holder, a video stylet, and a wireless adapter. The holder includes a mount configured to releasably secure the electronic device with a display, and an end cap, fixedly connected to the mount, defining a central cavity having a lower opening, the end cap configured to removably attach the holder to an upper end of a laryngoscope handle, the lower opening having a diameter conforming to a diameter of the upper end of the laryngoscope handle.

The video stylet includes one or more of a flexible segment including a flexible sheath enclosing a plurality of wires and a malleable segment including a malleable sheath having a smaller diameter than the flexible sheath, and a video camera coupled to one or more of the plurality of wires. The wireless adapter, coupled to one or more the holder and the video stylet, having a wireless communication capability and an electrical interface configured to communicate with a wireless network interface of a wireless network.

In another embodiment of the intubation system, the holder further including a shell configured to cover the end cap and coupled to the adjustable mount.

In another embodiment of the intubation system, the shell is configured to couple to a back side of the adjustable mount.

In another embodiment of the intubation system, a wireless adaptor of the holder having a wireless communication capability and an electrical interface configured to communicate with a wireless network interface of a wireless network.

In another embodiment of the intubation system, the wireless adaptor of the holder is coupled to one or more of the mount and the end cap of the holder.

In another embodiment of the intubation system, the wireless adaptor resides between and is coupled to the mount and the end cap of the holder.

In another embodiment of the intubation system, the wireless adaptor of the holder is integrated in one or more of the mount and the end cap.

In another embodiment of the intubation system, with a wireless adaptor of the video stylet having a wireless communication capability and an electrical interface configured to communicate with a wireless network interface of a wireless network, the wireless adaptor of the video stylet coupled to one or more of the flexible segment, the malleable segment and the video camera.

In another embodiment of the intubation system, the wireless adaptor of the video stylet is coupled to the camera at a distal end of video stylet.

In another embodiment of the intubation system, the holder and the video stylet are decoupled with a holder wireless adaptor of the holder in wireless communication with a video stylet wireless adaptor of the video outlet, the holder wireless adaptor configured to couple to a mounted electronic device with a display mounted in the mount.

In one embodiment a laryngoscope includes a handle portion; a blade portion coupled to the handle portion; a video stylet embedded within one or more of the handle portion and the blade portion; and a wireless adapter coupled to the video stylet having a wireless communication capability and an electrical interface configured to communicate with a wireless network interface of a wireless network.

In another embodiment of the laryngoscope, the wireless adapter is embedded within the handle and blade portions of the laryngoscope.

In another embodiment of the laryngoscope, the video stylet further comprising a camera disposed at a distal end of the blade portion, a flexible segment coupled to the camera, and a malleable segment coupled to the flexible segment and the wireless adapter at a proximal end of the video stylet.

In another embodiment of the laryngoscope, a power source of the handle wireless adapter is externally accessible to a user of the laryngoscope.

In another embodiment of the laryngoscope, the blade portion is a straight, curve, or variation blade portion.

In another embodiment of the laryngoscope, the wireless adapter is embedded within the handle and blade portions of the laryngoscope and a power source of the handle wireless adapter is externally accessible to a user of the laryngoscope.

In another embodiment of the laryngoscope, the blade portion of the laryngoscope handle is a straight or a curve blade portion.

In another embodiment of the laryngoscope, a blade portion and a handle portion of the laryngoscope handle are integrated parts of the laryngoscope and the handle wireless adapter is externally accessible to a user of the laryngoscope.

In another embodiment of the laryngoscope, the blade portion is a variation blade portion.

In another embodiment of the laryngoscope, the video camera is coupled to one or more of a plurality of wires of the flexible sheath of the flexible segment and the malleable sheath of the malleable segment.

In another embodiment of the laryngoscope, the malleable segment encloses a malleable wire and the plurality of wires.

In another embodiment of the laryngoscope, the video stylet further including a connecter, removably attachable to an electronic device and having built-in Wi-Fi capacity for wireless connection.

In another embodiment of the laryngoscope, the video style further including an additional connector, coupled to the plurality of wires, having an electrical interface configured to communicate with a wireless network interface of a wireless network.

In one embodiment, a laryngoscope enhancement system includes a holder and a video stylet. The holder includes an adjustable mount and an end cap. The adjustable mount is configured to releasably secure an electronic device with a display. The end cap is fixedly connected to the adjustable mount, and defines a central cavity with a lower opening. The end cap is configured to removably attach the holder to an upper end of a laryngoscope handle, and the lower opening has a diameter conforming to a diameter of the upper end of the laryngoscope handle. The video stylet includes a number of wires, a connecter coupled to the wires, a flexible segment, a malleable segment and a video camera coupled to one or more of the wires. The connector is removably attachable to an electronic device. The flexible segment includes a flexible sheath enclosing the wires. The malleable segment includes a malleable sheath enclosing a malleable wire and the wires. The malleable sheath has a smaller diameter than the flexible sheath.

In another embodiment of the laryngoscope enhancement system, the malleable wire extends along a length of the malleable segment.

In another embodiment of the laryngoscope enhancement system, the holder includes a guide configured to support the flexible segment of the video stylet.

In another embodiment of the laryngoscope enhancement system, the guide is disposed on an upper portion of the adjustable mount.

In another embodiment of the laryngoscope enhancement system, the guide is disposed on an upper portion of the end cap.

In another embodiment of the laryngoscope enhancement system, the video stylet further comprises an additional connector, coupled to the wires, having a different electrical interface than the connector.

In another embodiment of the laryngoscope enhancement system, the additional connector removably connectable to an additional electronic device.

In another embodiment of the laryngoscope enhancement system, the electronic device is a smart phone and the additional electronic device is a display.

In another embodiment of the laryngoscope enhancement system, the video stylet includes a light source coupled to at least one wire, and the flexible segment includes a light source control unit coupled to the least one wire.

In another embodiment of the laryngoscope enhancement system, the light source includes a plurality of light emitting diodes (LEDs) that surround a lens of the video camera.

In one embodiment, an intubation system includes an endotracheal tube (ETT), an electronic device with a display, and an enhanced laryngoscope. The ETT has an inner diameter. The enhanced laryngoscope includes a blade, a handle connected to the blade, a holder and a video stylet. The handle has an upper end and a diameter. The holder includes an adjustable mount and an end cap. The adjustable mount releasably secures the electronic device. The end cap defines a central cavity with a lower opening. The end cap is removably attached the upper end of the handle. The lower opening has a diameter conforming to the diameter of the handle. The video stylet includes a number of wires, a connecter coupled to the wires, a flexible segment, a malleable segment and a video camera coupled to one or more of the wires. The connector is removably attachable to the electronic device and, in some embodiments, has built-in wireless connectivity, such as Wi-Fi capacity for wireless connection. The flexible segment includes a flexible sheath enclosing the wires. The malleable segment includes a malleable sheath enclosing a malleable wire and the wires. The malleable sheath has a smaller diameter than the flexible sheath.

In another embodiment of the intubation system, the malleable wire extends along a length of the malleable segment.

In another embodiment of the intubation system, the holder includes a guide configured to support the flexible segment of the video stylet.

In another embodiment of the intubation system, the guide is disposed on an upper portion of the adjustable mount.

In another embodiment of the intubation system, the guide is disposed on an upper portion of the end cap.

In another embodiment of the intubation system, the video stylet further comprises an additional connector, coupled to the wires, having a different electrical interface than the connector.

In another embodiment of the intubation system, the additional connector removably connectable to an additional electronic device.

In another embodiment of the intubation system, the electronic device is a smart phone and the additional electronic device is a display.

In another embodiment of the intubation system, the video stylet includes a light source coupled to at least one wire, and the flexible segment includes a light source control unit coupled to the least one wire.

In another embodiment of the intubation system, the light source includes a plurality of light emitting diodes (LEDs) that surround a lens of the video camera.

While implementations of the disclosure are susceptible to embodiment in many different forms, there is shown in the drawings and will herein be described in detail specific embodiments, with the understanding that the present disclosure is to be considered as an example of the principles of the disclosure and not intended to limit the disclosure to the specific embodiments shown and described. In the description above, like reference numerals may be used to describe the same, similar or corresponding parts in the several views of the drawings.

In this document, relational terms such as first and second, top and bottom, and the like may be used solely to distinguish one entity or action from another entity or action without necessarily requiring or implying any actual such relationship or order between such entities or actions. The terms “comprises,” “comprising,” “includes,” “including,” “has,” “having,” or any other variations thereof, are intended to cover a non-exclusive inclusion, such that a process, method, article, or apparatus that comprises a list of elements does not include only those elements but may include other elements not expressly listed or inherent to such process, method, article, or apparatus. An element preceded by “comprises . . . a” does not, without more constraints, preclude the existence of additional identical elements in the process, method, article, or apparatus that comprises the element.

Reference throughout this document to “one embodiment,” “certain embodiments,” “an embodiment,” “implementation(s),” “aspect(s),” or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The term “or” as used herein is to be interpreted as an inclusive or meaning any one or any combination. Therefore, “A, B or C” means “any of the following: A; B; C; A and B; A and C; B and C; A, B and C.” An exception to this definition will occur only when a combination of elements, functions, steps or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term “or” should generally be understood to mean “and/or” and so forth. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated, and each separate value within such a range is incorporated into the specification as if it were individually recited herein. The words “about,” “approximately,” or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language (“e.g.,” “such as,” “for example,” or the like) provided herein, is intended merely to better illuminate the embodiments and does not pose a limitation on the scope of the embodiments. No language in the specification should be construed as indicating any unclaimed element as essential to the practice of the embodiments.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

In the following description, it is understood that terms such as "first," "second," "top," "bottom," "up," "down," "above," "below," and the like, are words of convenience and are not to be construed as limiting terms. Also, the terms apparatus, device, system, etc. may be used interchangeably in this text.

The many features and advantages of the disclosure are apparent from the detailed specification, and, thus, it is intended by the appended claims to cover all such features and advantages of the disclosure which fall within the scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

What is claimed is:

1. A laryngoscope enhancement system, comprising:
- a holder, including:
  - a mount configured to releasably secure an electronic device with a display, and
  - an end cap, fixedly connected to the mount, defining a central cavity having a lower opening, the end cap configured to removably attach the holder to an upper end of a laryngoscope handle, the lower opening having a diameter conforming to a diameter of the upper end of the laryngoscope handle; and
- a video stylet, including:
  - a plurality of wires,
  - a connecter, coupled to the plurality of wires, removably attachable to the electronic device, the connector having built-in Wi-Fi capability for wireless connection;
  - an additional connector, coupled to the plurality of wires, having an electrical interface configured to communicate with a wireless network interface of a wireless network;
  - a flexible segment including a flexible sheath enclosing the plurality of wires,
  - a malleable segment including a malleable sheath enclosing a malleable wire and the plurality of wires, the malleable sheath having a smaller diameter than the flexible sheath, and
  - a video camera coupled to one or more of the plurality of wires.

2. The system according to claim 1, where the additional connector has a different electrical interface than the connector.

3. The system according to claim 2, where the additional connector is removably connectable to an additional electronic device.

4. The system according to claim 3, where the electronic device is a smart phone and the additional electronic device is a display.

5. The system according to claim 1, where the video stylet includes a light source coupled to at least one of the plurality of wires, and the flexible segment includes a light source control unit coupled to the at least one of the plurality of wires.

6. The system according to claim 5, where the light source includes a plurality of light emitting diodes that surround a lens of the video camera.

7. The system according to claim 1, where the additional connector is configured to communicate with one or more of a Wi-Fi network interface of the electronic device and a Wi-Fi network interface of an additional electronic device.

8. An intubation system, comprising:
- an endotracheal tube having an inner diameter;
- an electronic device with a display; and
- a laryngoscope, including:
  - a blade,
  - a handle, connected to the blade, having an upper end and a diameter,
  - a holder, including:
    - a mount releasably securing the electronic device, and
    - an end cap defining a central cavity having a lower opening, the end cap removably attached to the upper end of the handle, the lower opening having a diameter conforming to the diameter of the handle, and
  - a video stylet, including:
    - a plurality of wires,
    - a connecter, coupled to the plurality of wires, removably attachable to the electronic device, the connector having built-in Wi-Fi capability for wireless connection;
    - an additional connector, coupled to the plurality of wires, having an electrical interface configured to communicate with a wireless network interface of a wireless network,
    - a flexible segment including a flexible sheath enclosing the plurality of wires,
    - a malleable segment including a malleable sheath enclosing a malleable wire and the plurality of wires, the malleable sheath having a smaller diameter than the flexible sheath, and
    - a video camera coupled to one or more of the plurality of wires.

9. The system according to claim 8, where the additional connector has a different electrical interface than the connector.

10. The system according to claim 8, where the additional connector is removably connectable to an additional electronic device.

11. The system according to claim 10, where the electronic device is a smart phone and the additional electronic device is a display.

12. The system according to claim 8, where the video stylet includes a light source coupled to at least one of the plurality of wires, and the flexible segment includes a light source control unit coupled to the at least one of the plurality of wires.

13. The system according to claim 8, where the additional connector is configured to communicate with one or more of a Wi-Fi network interface of the electronic device and a Wi-Fi network interface of an additional electronic device.

14. A laryngoscope enhancement system, comprising:
- a holder, including:
  - a mount configured to releasably secure an electronic device with a display, and
  - an end cap, fixedly connected to the mount, defining a central cavity having a lower opening, the end cap configured to removably attach the holder to an upper end of a laryngoscope handle, the lower opening having a diameter conforming to a diameter of the upper end of the laryngoscope handle;
- a video stylet, including:
  - one or more of a flexible segment including a flexible sheath enclosing a plurality of wires and a malleable segment including a malleable sheath having a smaller diameter than the flexible sheath, and a video camera coupled to one or more of the plurality of wires; and a wireless adapter, coupled to one or more of the holder and the video stylet and when coupled to the holder the wireless adapter is coupled to one or more of the mount and the end cap of the holder, having a wireless communication capability and an electrical interface configured to communicate with a wireless network interface of a wireless network.

15. The laryngoscope enhancement system of claim 14, the holder further including a shell configured to cover the end cap and coupled to the mount.

16. The laryngoscope enhancement system of claim 15, where the shell is configured to couple to a back side of the mount.

17. The laryngoscope enhancement system of claim 14, where the wireless adapter resides between and is coupled to the mount and the end cap of the holder.

18. The laryngoscope enhancement system of claim 14, where the wireless adapter of the holder is integrated in one or more of the mount and the end cap.

19. The laryngoscope enhancement system of claim 14, where the wireless adapter of the video stylet is coupled to one or more of the flexible segment, the malleable segment and the video camera.

20. The laryngoscope enhancement system of claim 19, where the wireless adapter of the video stylet is coupled to the video camera at a distal end of the video stylet.

21. The laryngoscope enhancement system of claim 14, where the holder and the video stylet are not physically connected, with a holder wireless adapter of the holder in wireless communication with a video stylet wireless adapter of the video stylet, the holder wireless adapter configured to couple to a mounted electronic device with a display mounted in the mount.

22. An intubation system, comprising:

an endotracheal tube having an inner diameter;

an electronic device with a display; and a laryngoscope, including:

a blade, a handle, connected to the blade, having an upper end and a diameter, a holder, including:

a mount configured to releasably secure the electronic device with the display, and an end cap, fixedly connected to the mount, defining a central cavity having a lower opening, the end cap configured to removably attach the holder to the upper end of the laryngoscope handle, the lower opening having a diameter conforming to a diameter of the upper end of the laryngoscope handle;

a video stylet, including:

one or more of a flexible segment including a flexible sheath enclosing a plurality of wires and a malleable segment including a malleable sheath having a smaller diameter than the flexible sheath, and a video camera coupled to one or more of the plurality of wires; and a wireless adapter, coupled to one or more of the holder including one or more of the mount and the end cap of the holder and the video stylet, having a wireless communication capability and an electrical interface configured to communicate with a wireless network interface of a wireless network.

23. The intubation system of claim 22, the holder further including a shell configured to cover the end cap and coupled to the mount.

24. The intubation system of claim 23, where the shell is configured to couple to a back side of the mount.

25. The intubation system of claim 22, where the wireless adapter resides between and is coupled to the mount and the end cap of the holder.

26. The intubation system of claim 22, where the wireless adapter of the holder is integrated in one or more of the mount and the end cap.

27. The intubation system of claim 22, where the wireless adapter of the video stylet is coupled to one or more of the flexible segment, the malleable segment and the video camera.

28. The intubation system of claim 27, where the wireless adapter of the video stylet is coupled to the video camera at a distal end of the video stylet.

29. The intubation system of claim 22, where the holder and the video stylet are not physically connected, with a holder wireless adapter of the holder in wireless communication with a video stylet wireless adapter of the video stylet, the holder wireless adapter configured to couple to a mounted electronic device with a display mounted in the mount.

30. A laryngoscope comprising:

a handle portion and a blade portion together forming a single wireless blade with embedded wireless capability;

an endotracheal tube embedded within at least the blade portion, the endotracheal tube comprising a distal end with a light source and a camera disposed near a tip of the blade portion; and a wireless adapter, coupled to a proximal end of the endotracheal tube and embedded within at least the handle portion, having a wireless communication capability and an electrical interface configured to communicate with a wireless network interface of a wireless network, the wireless adapter having a power actuator externally accessible to a user of the laryngoscope on the handle portion.

31. The laryngoscope of claim 30, where the blade portion is a straight blade portion, a curve blade portion, or a variation blade portion.

32. The laryngoscope of claim 30, where the blade portion is a straight blade portion or a curve blade portion.

33. The laryngoscope of claim 30, where the blade portion and the handle portion are integrated parts of the laryngoscope.

34. The laryngoscope of claim 33, where the blade portion is a variation blade portion.

35. The laryngoscope of claim 30, where the camera is coupled to one or more of a plurality of wires of a flexible sheath of the flexible segment and a malleable sheath of the malleable segment.

36. The laryngoscope of claim 35, where the malleable segment encloses a malleable wire and the plurality of wires.

37. The laryngoscope of claim 35, the video stylet further including a connecter, removably attachable to an electronic device and having built-in Wi-Fi capability for wireless connection.

38. The laryngoscope of claim 37, the video stylet further including an additional connector, coupled to the plurality of wires, the electrical interface configured to communicate with the wireless network interface of the wireless network.

* * * * *